United States Patent [19]
Wolf et al.

[11] Patent Number: 5,990,079
[45] Date of Patent: Nov. 23, 1999

[54] AGENTS AFFECTING THROMBOSIS AND HEMOSTASIS

[75] Inventors: David L. Wolf, Palo Alto; Uma Sinha, San Francisco, both of Calif.

[73] Assignee: COR Therapeutics Inc., South San Francisco, Calif.

[21] Appl. No.: 09/016,400

[22] Filed: Jan. 30, 1998

Related U.S. Application Data

[60] Continuation of application No. 08/469,301, Jun. 6, 1995, Pat. No. 5,837,679, which is a division of application No. 08/268,003, Jun. 29, 1994, Pat. No. 5,583,107, which is a continuation-in-part of application No. 08/249,777, May 26, 1994, Pat. No. 5,597,799, which is a continuation of application No. 07/808,329, Dec. 16, 1991, abandoned, which is a continuation-in-part of application No. 07/578,646, Sep. 4, 1990, Pat. No. 5,278,144.

[51] Int. Cl.$^6$ .......................... A61K 38/36; A61K 35/16; A61F 13/00; C07K 14/435

[52] U.S. Cl. .......................... 514/2; 424/94.64; 424/422; 424/423; 435/212; 530/381; 530/384; 530/830

[58] Field of Search .................................. 514/2, 12, 21, 514/834, 8; 530/380, 381, 384, 350, 407, 829, 830, 831, 395; 435/69.1, 69.2, 69.6, 212; 424/94.64, 422, 426, 423, 428

[56] References Cited

U.S. PATENT DOCUMENTS

| | | | |
|---|---|---|---|
| 4,337,244 | 6/1982 | Smith | 424/94.64 |
| 4,382,083 | 5/1983 | Thomas | 474/94.64 |
| 4,604,285 | 8/1986 | Faith et al. | 474/94.6 |
| 4,970,300 | 11/1990 | Fulton et al. | 530/383 |
| 5,114,851 | 5/1992 | Porter et al. | 435/440 |
| 5,278,144 | 1/1994 | Wolf | 514/12 |
| 5,583,107 | 12/1996 | Wolf et al. | 514/12 |
| 5,597,799 | 1/1997 | Wolf | 514/12 |
| 5,837,679 | 11/1998 | Wolf et al. | 514/12 |

FOREIGN PATENT DOCUMENTS

9204378  3/1992  WIPO.

OTHER PUBLICATIONS

Bernardi, et al., "Partial Gene Deletion in a Family with Factor X Deficiency" *Blood*, vol. 73, No. 8, 2123–2127 (1989).

Cassels, et al., "The Interaction of Streptokinase Plasminogen Activator Complex, Tissue–Type Plasminogen Activator, Urokinase and their Acylated Derivatives with Fibrin and Cyanogen Bromide Digest of Fibrinogen" *Biochem. J.* 247, 395–400 (1987).

Crabbe, et al., "Acylated Plasminogen–Streptokinase Activator Complex: A New Approach to Thrombolytic Therapy" *Pharmacotherapy*, vol. 10, No. 2, 115–126 (1990).

Davie, "The Blood Coagulation Factors: Their cDNAs, Genes, and Expression" *Plasma Coagulation Factors*, 242–267.

DiScipio, et al., "Activation of Human Factor X (Stuart Factor) by a Protease from Russell's Viper Venom" *Biochemistry*, vol. 6, No. 24, 5253–5260 (1977).

Dunwiddie, et al., "Antistasin, a Leech–Derived Inhibitor of Factor Xa" *The Journal of Biological Chemistry*, vol. 264, No. 26, 16694–16699 (1989).

Etingin, et al., "Viral Activation of the Coagulation Cascade: Molecular Interactions at the Surface of Infected Endothelial Cells" *Cell*, vol. 61, 657–662 (1990).

Fair, et al., "Isolation and Characterization of the Factor X Friuli Variant" *Blood*, vol. 73, No. 8, 2108–2116 (1989).

Fears, "Development of Anisoylated Plasminogen–Streptokinase Activator Complex from the Acyl Enzyme Concept" *Seminars in Thrombosis and Hemostasis–Vol. 15*, No. 2, 129–139 (1989).

Fears, et al., "The Protective Effect of Acylation on the Stability of Anisoylated Plasminogen Streptokinase Activator Complex in Human Plasma" *Drugs 33 (Suppl. 3*, 57–63 (1987).

Furie, et al., "The Molecular Basis of Blood Coagulation" *Cell*, vol. 53, 505–518 (1988).

Girard, et al., "Functional Significance of the Kunitz–Type Inhibitory Domains of Lipoprotein–Associated Coagulation Inhibitor" *Nature*, vol. 338, 518–520 (1989).

Girard, et al., "Inhibition of Factor VIIa–Tissue Factor Coagulation Activity by a Hybrid Protein" *Science*, vol. 248, 1421–1424 (1990).

Hassan, et al., "Multiple Polymorphic Sites in Factor X Locus" *Blood*, vol. 71, No. 5, 1353–1356 (1988).

Hoover, et al., "The Adhesive Interaction between Polymorphonuclear Leukocytes and Endothelial Cells in Vitro" *Cell*, vol. 14, 423–428 (1978).

Husten, et al., "The Active Site of Blood Coagulation Factor Xa" *The Journal of Biological Chemistry*, vol. 262, No. 27, 12953–12961 (1987).

Krishnaswamy, et al., "Prothrombinase Complex Assembly" *The Journal of Biological Chemistry*, vol. 263, No. 8, 3823–3834 (1988).

Levine, "Clinical Manifestations and Therapy of Hemophilias A and B" *Plasma Coagulation Factors*, 97–111.

Nesheim, et al., "The Contribution of Bovine Factor V and Factor Va to the Activity of Prothrombinase" *The Journal of Biological Chemistry*, vol. 254, No. 21, 10952–10962 (1979).

Nesheim, et al., "Cofactor Dependence of Factor Xa Incorporation into the Prothrombinase Complex" *The Journal of Biological Chemistry*, vol. 256, No. 13, 6537–6540 (1981).

Reddy, et al., "Molecular Characterization of Human Factor $X_{San\ Antonio}$" *Blood*, vol. 74, No. 5, 1486–1490 (1989).

(List continued on next page.)

*Primary Examiner*—Nancy Degen
*Attorney, Agent, or Firm*—Morgan, Lewis & Bockius LLP

[57] ABSTRACT

Analogs of blood factors which are transiently inactive are useful in treatment of diseases characterized by thrombosis. In addition, modified forms of activated blood factors that generate the active blood factor in serum but have extended half-lives are useful in treating hemophilia conditions. These modified forms of the blood factor may be acylated forms which are slowly deacylated in vivo.

16 Claims, 15 Drawing Sheets

OTHER PUBLICATIONS

Skogen, et al., "Comparison of Coagulation Factor Xa and Des–(1–44) Factor Xa in the Assembly of Prothrombinase" *The Journal of Biological Chemistry*, vol. 256, No. 4, 2306–2310 (1984).

Steinberg, et al., "Activation of Factor X" *Plasma Coagulation Factors*, 112–119.

Stürzebecher, et al., "Stable Acyl–Derivatives of Tissue–Type Plasminogen Activator" *Thrombosis Research 47*, 699–703 (1987).

Watzke, et al., Molecular Defect ($Gla^{+14} \rightarrow Lys$) and its Functional Consequences in a Hereditary Factor X Deficiency (Factor X "Vorarlberg") *The Journal of Biological Chemistry*, vol. 285, No. 20, 11982–11989 (1990).

Waxman, et al., "Tick Anticoagulant Peptide (TAP) is a Novel Inhibitor of Blood Coagulation Factor Xa" *Science*, vol. 248, 593–596 (1990).

Neuenschwander et al Anal Biochem. 184 347–352 1990.

Nucir et al Adv. Drug Del. Rev 6 133–151 1991.

Fuy et al PNAS 82 3591–3595 1985.

Parrish, "New Concepts In Therapeutic Photomedicine: Photochemistry, Optical Targeting & The Therapeutic Window" J Invest Dermatol. 77(1) 45–50, Jul. 1981.

| | | | | |
|---|---|---|---|---|
| 1 | GTCGACTCTA | GAGGGGCTGG | CAGGAATTCC | GCATGGGGCG | CCCACTGCAC |
| 51 | CTCGTCCTGC | TGAGTGCCTG | CCTGGCTGGC | CTCCTGCTGC | TCGGGGAAAG |
| 101 | TCTGTTCATC | CGCAGGGAGC | AGGCCAACAA | CATCCTGGCG | AGGGTCACGA |
| 151 | GGGCCAATTC | CTTTCTTGAA | GAGATGAAGA | AAGGACACCT | CGAAAGAGAG |
| 201 | TGCATGGAAG | AGACCTGCTC | ATACGAAGAG | GCCCGCGAGG | TCTTTGAGGA |
| 251 | CAGCGACAAG | ACGAATGAAT | TCTGGAATAA | ATACAAAGAT | GGCGACCAGT |
| 301 | GTGAGACCAG | TCCTTGCCAG | AACCAGGGCA | AATGTAAAGA | CGGCCTCGGG |
| 351 | GAATACACCT | GCACCTGTTT | AGAAGGATTC | GAAGGCAAAA | ACTGTGAATT |
| 401 | ATTCACACGG | AAGCTCTGCA | GCCTGGACAA | CGGGGACTGT | GACCAGTTCT |
| 451 | GCCACGAGGA | ACAGAACTCT | GTGGTGTGCT | CCTGCGCCCG | CGGGTACACC |
| 501 | CTGGCTGACA | ACGGCAAGGC | CTGCATTCCC | ACAGGGCCCT | ACCCCTGTGG |
| 551 | GAAACAGACC | CTGGAACGCA | GGAAGAGGTC | AGTGGCCCAG | GCCACCAGCA |
| 601 | GCAGCGGGGA | GGCCCCTGAC | AGCATCACAT | GGAAGCCATA | TGATGCAGCC |
| 651 | GACCTGGACC | CCACCGAGAA | CCCCTTCGAC | CTGCTTGACT | TCAACCAGAC |
| 701 | GCAGCCTGAG | AGGGGCGACA | ACAACCTCAC | CAGGATCGIG | GGAGGCCAGG |
| 751 | AATGCAAGGA | CGGGGAGTGT | CCCTGGCAGG | CCCTGCTCAT | CAATGAGGAA |
| 801 | AACGAGGGTT | TCTGTGGTGG | AACTATTCTG | AGCGAGTTCT | ACATCCTAAC |
| 851 | GGCAGCCCAC | TGTCTCTACC | AAGCCAAGAG | ATTCAAGGTG | AGGTAAGGGG |
| 901 | ACCGGAACAC | GGAGCAGGAG | GAGGGCGGTG | AGGCGGTGCA | CGAGGTGGAG |
| 951 | GTGGTCATCA | AGCACAACCG | GTTCACAAAG | GAGACCTATG | ACTTCGAGAT |
| 1001 | CGCCGTGCTC | CGGCTCAAGA | CCCCCATCAC | CTTCCGCATG | AACGTGGCGC |
| 1051 | CTGCCTGCCT | CCCCGAGCGT | GACTGGGCCG | AGTCCACGCT | GATGACGCAG |
| 1101 | AAGACGGGGA | TTGTGAGCGG | CTTCGGCGC | ACCCACGAGA | AGGGCCGGCA |
| 1151 | GTCCACCAGG | CTCAAGATGC | TGGAGGTGCC | CTACGTGGAC | CGCAACAGCT |
| 1201 | GCAAGCTGTC | CAGCAGCTTC | ATCATCACCC | AGAACATGTT | CTGTGCCGGC |
| | | | | | |
| 1301 | CGTCACCCGC | TTCAAGGACA | CCTACTTCGT | GACAGGCATC | GTCAGCTGGG |
| 1351 | GAGAGGGCTG | TGCCCGTAAG | GGGAAGTACG | GGATCTACAC | CAAGGTCACC |
| 1401 | GCCTTCCTCA | AGTGGATCGA | CAGGTCCATG | AAAACCAGGG | GCTTGCCCAA |
| 1451 | GGCCAAGAGC | CATGCCCCGG | AGGTCATAAC | GTCCTCTCCA | TTAAAGTGAG |
| 1501 | CGTCCTCTCC | ATCCCACTCA | AAAAAAAAAA | AAAAAAAAAA | AAAAAAAAA |

Fig. 4

AGENTS AFFECTING THROMBOSIS AND HEMOSTASIS

This application is a continuation of Ser. No. 08/469,301, filed Jun. 6, 1995, now U.S. Pat. No. 5,837,679, which is a divisional application of Ser. No. 08/268,003, filed Jun. 29, 1994, now U.S. Pat. No. 5,583,107, which is a continuation-in-part of Ser. No. 08/249,777, filed May 26, 1994, now U.S. Pat. No. 5,597,799, which is a continuation of Ser. No. 07/808,329, filed Dec. 16, 1991, now abandoned, which is a continuation-in-part of Ser. No. 07/578,646, filed Sep. 4, 1990 and now U.S. Pat. No. 5,278,144.

TECHNICAL FIELD

The invention relates to peptide drugs for regulation of hemostatic and thrombotic processes. The invention also concerns coagulation factors whose protease or enzymatic activity has been transiently inactivated.

BACKGROUND ART

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. After initiation of clotting, blood coagulation proceeds through the sequential activation of certain plasma proenzymes to their enzyme forms. These plasma glycoproteins, including Factor XII, Factor XI, Factor IX, Factor X, Factor VII, and prothrombin, are zymogens of serine proteases. Most of these blood clotting enzymes are effective on a physiological scale only when assembled in complexes on membrane surfaces with protein cofactors such as Factor VIII and Factor V. Other blood factors modulate and localize clot formation, or dissolve blood clots. Activated protein C is a specific enzyme that inactivates procoagulant components. Calcium ions are involved in many of the component reactions. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Thrombin is a multifunctional protease that regulates several key biological processes. For example thrombin is among the most potent of the known platelet activators. In addition, as described above, thrombin is essential for the cleavage of fibrinogen to fibrin to initiate clot formation. These two elements are involved in normal hemostasis but in atherosclerotic arteries can initiate the formation of a thrombus, which is a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth cell proliferation and may therefore be involved in a variety of proliferative responses such as restenosis after angioplasty and graft induced atherosclerosis. In addition, thrombin is chemotactic for leukocytes and may therefore play a role in inflammation. (Hoover, R. J., et al. *Cell* (1978) 14:423; Etingin, O. R., et al., Cell (1990) 61:657.) These observations indicate that inhibition of thrombin formation or inhibition of thrombin itself may be effective in preventing or treating thrombosis, limiting restenosis and controlling inflammation.

The formation of thrombin is the result of the proteolytic cleavage of its precursor prothrombin at the Arg-Thr linkage at positions 271–272 and the Arg-Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kd precursor and is converted to the active form, Factor Xa, in both the extrinsic and intrinsic blood coagulation pathways. It is known that the circulating levels of Factor X, and of the precursor of Factor Va, Factor V, are on the order of $10^{-7}$ M. There has been no determination of the levels of the corresponding active Factors Va and Xa.

The amino acid sequences and genes of most of the plasma proteins involved in hemostasis of blood have been determined, including Factor VIIa, Factor IXa, Activated Protein C, Factor X and Factor Xa. FIG. 1 shows the complete sequence of the precursor form of Factor X as described by Davie, E. W., in *Hemostasis and Thrombosis,* Second Edition, R. W. Coleman et al. eds. (1987) p. 250. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., *Cell* (1988) 53:505).

As shown in FIG. 1, the mature Factor X protein is preceded by a 40-residue pre-pro leader sequence which is removed during intracellular processing and secretion. The mature Factor X precursor of Factor Xa is then cleaved to the two-chain form by deletion of the three amino acids RKR shown between the light chain C-terminus and activation peptide/heavy chain N-terminus. Finally, the two chain Factor X is converted to Factor Xa by deletion of the "activation peptide" sequence shown at the upper right-hand portion of the figure (numbered 1–52), generating a light chain shown as residues 1–139, and a heavy chain shown as residues 1–254. These are linked through a single disulfide bond between position 128 of the light chain and position 108 of the heavy chain. As further indicated in the figure, the light chain contains the Gla domain and a growth factor domain; the protease activity resides in the heavy chain and involves the histidine at position 42, the aspartic at position 88, and a serine at position 185, circled in the figure.

There are two known pathways for the activation of the two-chain Factor X in vivo. Activation must occur before the protease is incorporated into the prothrombinase complex (Steinberg, M., et al., in *Hemostasis and Thrombosis,* Coleman, R. W., et al. eds. (1987) J. B. Lippencott, Philadelphia, Pa., p. 112). In the intrinsic pathway, Factor X is cleaved to release the 52-amino acid activation peptide by the "tenase" complex which consists of Factor IXa, Factor VII and calcium ions assembled on cell surfaces. In the extrinsic pathway, the cleavage is catalyzed by Factor VIIa which is bound to a tissue factor on membranes. Also of interest herein is the ability to convert Factor X to Factor Xa by in vitro cleavage using a protease such as that contained in Russell's viper venom. This protease is described by DiScipio, R. G., et al., *Biochemistry* (1977) 6:5253.

In some circumstances, it is desirable to interfere with the functioning of Factor Xa in order to prevent excessive clotting. However in others, such as in hemophilia, it is desirable to provide a source of Factor Xa independent of the activation process that takes place in normal individuals. Both of the common forms of hemophilia involve deficiencies in only the intrinsic pathway of activation, but the operation of the extrinsic pathway does not appear to be successful in arresting bleeding.

The most common forms of hemophilia are hemophilia A which reflects a deficiency in the functioning of Factor VII, and hemophilia B which reflects a deficiency in the functioning of Factor IX (also known as Christmas factor). These forms of hemophilia are well known. Similarly, other patients are treated currently for deficiencies of other blood factors (VII, X, XI, XIII) or von Willebrand's disease. Factor VII deficiency is not as clinically well-defined as hemophilia A or B, however patients with Factor VII deficiency have been reported to have extensive bleeding. Protein C deficiency is associated with thrombotic risk.

Currently hemophiliacs (and other individuals with factor deficiencies) are treated with clotting (or other blood) factors on a prophylactic basis, however current treatment strategies are not entirely satisfactory. It is known for example that large numbers of hemophilia patients develop inhibitors to clotting factors, and these patients are then treated with products known as "bypass factors", such as Factor VII or Factor IX complexes, or activated Factor IX complexes, or factors from other mammalian species, such as porcine Factor VII. In turn, some bypass factors have disadvantages, such as being thrombogenic (especially in immobile patients), or by lack of specificity. Even in the same patient, it has been shown that these therapies can be reliable on one administration and not effective on another (Lusher, J. M., Management of Hemophiliacs with Inhibitors, Hemophilia in the Child and Adult, M. Hilgartner and C. Pochedly, eds., New York, Raven Press, 1989.).

There exists a need for improved treatments for hemophilia and other blood factor deficiencies.

For hemophilia patients, since a deficiency in either of factors VIII or IX result in an inadequate supply of Factor Xa, provision of Factor Xa should be effective in treatment of both hemophilias. In addition, a number of instances have been found wherein Factor X itself is incapable of providing an active Factor Xa. This relatively rare class of congenital disorders has been described, for example, by Reddy, S. B., et al., *Blood* (1989) 74:1486–1490; Watzke, H. H., et al. *J Biol Chem* (1990) 2:11982–11989; Hassan, H. J., et al., *Blood* (1988) 71:1353–1356; Fair, D. S., et al., *Blood* (1989) 73:2108–2116; and by Bernardi, F., et al., *Blood* (1989) 73:2123–2127.

Factor Xa, and several other activated blood factors, have not heretofore been useful as pharmaceuticals because of their extremely short half-life in serum, which for example typically is only about 30 seconds for Factor Xa. In the invention described below, the half-life of these agents in serum is extended by providing a transiently inactivated, slow release form, preferably an acylated form. In certain embodiments relating to Factor X, an acyl group is bound to the serine at the active site and inhibits clearance and is only slowly hydrolyzed to generate the active form of Factor Xa. In similar fashion, this invention also relates to other transiently inactivated blood factors, including activated Protein C, Factor IXa and Factor VIIa.

The use of acylation to prolong the half-life of certain blood clotting factors has been disclosed. For example, Cassels, R. et al. *Biochem J* (1987) 247:359–400 found that various acylating agents remained bound to urokinase, tPA and streptokinase-plasminogen activator complex for time periods ranging from a half-life of 40 minutes to a half-life of over 1,000 minutes depending on the nature of the acylating group and the nature of the factor. Acylation of tPA or streptokinase is also disclosed in U.S. Pat. No. 4,337,244. The use of an amidinophenyl group functioning as an arginine analog to introduce, temporarily, a substituted benzoyl group into the active site for the purpose of enhancing serum stability was discussed by Fears, R. et al., *Seminars in Thrombosis and Homeostasis* (1989) 15:129–139. This more general review followed a short report by Fears, R. et al. in *Drugs* (1987) 33: Supp. 3 57–63. Sturzebecher, J. et al. also reported stabilized acyl derivatives of tPA in *Thrombosis Res* (1987) 47:699–703. An additional report of the use of the acylated plasminogen streptokinase activator complex (APSAC) was published by Crabbe, S. J. et al. *Pharmacotherapy* (1990) 10:115–126. Acylated forms of thrombin have also been described.

Returning to the function of Factor Xa per se, the activity of Factor Xa in effecting the conversion of prothrombin to thrombin is dependent on its inclusion in the prothrombinase complex. The formation of the prothrombinase complex (which is 278,000 fold faster in effecting the conversion of prothrombin to thrombin than Factor Xa in soluble form) has been studied (Nesheim, H. E., et al., *J Biol Chem* (1979) 254:10952). These studies have utilized the active site-specific inhibitor, dansyl glutamyl glycyl arginyl (DEGR) chloromethyl ketone, which covalently attaches a fluorescent reporter group into Factor Xa. Factor Xa treated with this inhibitor lacks protease activity, but is incorporated into the prothrombinase complex with an identical stoichiometry to that of Factor Xa and has a dissociation constant of $2.7 \times 10^{-6}$ M (Nesheim, M. E., *J Biol Chem* (1981) 256:6537–6540; Skogen, W. F., et al., *J Biol Chem* (1984) 256:2306–2310; Krishnaswamy, S., et al., *J Biol Chem* (1988) 263:3823–3824; Husten, E. J., et al., *J Biol Chem* (1987) 262:12953–12961).

Known methods to inhibit the formation of the prothrombinase complex include treatment with heparin and heparin-like compounds. This results in inhibition of the formation of the complex by antithrombin III in association with the heparin. Other novel forms of Factor Xa inhibition include lipoprotein-associated coagulation inhibitor (LACI) (Girard, T. J., et al., *Nature* (1989) 383:518; Girard, T. J., et al., *Science* (1990) 248:1421), leech-derived antistatin (Donwiddie, C., et al., *J Biol Chem* (1989) 264:16694), and tick-derived TAP (Waxman, L., et al., *Science* (1990) 248:593). Alternatively, agents which inhibit the vitamin K-dependent Gla conversion enzyme, such as coumarin, have been used. None of these approaches have proved satisfactory due to lack of specificity, the large dosage required, toxic side effects, and the long delay in effectiveness.

DISCLOSURE OF THE INVENTION

The invention provides effective therapeutic agents for the regulation of hemostasis, and for the prevention and treatment of thrombus formation and other pathological processes in the vasculature induced by thrombin such as restenosis and inflammation. This is highly significant as thrombus formation is the leading cause of death in Western societies, and restenosis is an expanding problem with increased use of angioplasty and other invasive procedures.

The therapeutic materials of the invention are inactive (either permanently or transiently) forms of mammalian blood factors including Factor IXa, Factor VIIa, activated Protein C, and Factor Xa.

Certain aspects of this invention relate to permanently inactive forms of Factor Xa which are nevertheless capable of incorporation prothrombinase complex, thus preventing the formation of active prothrombinase complex from endogenous Factor Xa. These pharmaceuticals are especially useful in acute settings to prevent thrombosis. This includes preventing thrombus formation in the coronary arteries of patients with rest angina, preventing rethrombosis after thrombolysis, and prevention of thrombosis during complicated angioplasties. These pharmaceuticals will also be useful in preventing smooth muscle cell proliferation following angioplasty or other vascular invasive procedures. The invention therapeutics offer considerable advantage over the now standard treatment which involves heparin (Hanson, R. S., et al., *Proc Nat Acad Sci* (1988) 85:3184). The compounds of certain aspects of this invention are double- or single-chain polypeptides which are capable of participation in the prothrombinase complex, but which result in an inactive complex.

In one aspect, the invention is directed to a two-chain polypeptide, designated Factor Xai, which is capable of forming the prothrombinase complex, but which results in a complex that lacks proteolytic activity. This two-chain polypeptide may be formed from one of two types of novel precursors. One type, designated herein Factor Xi, has substantially the amino acid sequence of Factor X, but is modified as described herein so as to result in an inactive two-chain polypeptide, Factor Xai, when cleaved by normal coagulation processing proteases or by in vitro treatment with Factor X activator from viper venom. The other type, designated herein Factor X'i, is a truncated form of single chain Factor X wherein the proteolytic cleavage site (or portion or extension thereof) at the C-terminus of the light chain, shown as RXR in FIG. 1, is ligated directly (with the optional addition of one or several amino residues) to the N-terminus of the activated form of the heavy chain as shown in one embodiment in FIG. 3. Upon cleavage, Factor X'i also results in the two-chain Factor Xai of the invention which results in a prothrombinase complex lacking proteolytic activity. Of course, the active cofactor, Factor Xa, could also be generated by using the analogous precursors of the Factor X' type illustrated in FIG. 2.

Thus, in other aspects, the invention is directed to the Factor Xai two-chain prothrombinase complex, and to the novel precursors of the Factor Xai therapeutic proteins, to the DNA sequences encoding them, and to recombinant materials and methods generally which permit their production.

Other aspects of the invention include pharmaceutical compositions of the therapeutically useful Factor Xai proteins and to methods to prevent or treat thrombosis or other pathological events initiated by thrombin using these compositions. In certain other aspects of this invention, transiently inactivated blood proteins such as activated Protein C are used as antithrombotics, where controlled, slow-release formulations are desired.

This invention is also directed to transiently inactivated blood factors which are suitable for use as procoagulents, such as for wound healing, as bypass factors or in replacement therapy, or other treatments for hemophilia.

The availability of recombinantly produced and plasma derived blood factors provides a convenient source for these materials for use as procoagulants, antithrombotics, or in the treatment of hemophilia. For example, in the practice of this invention, Factor Xa, whether recombinantly produced directly, obtained from recombinantly produced Factor X by activation using, for example, Russell's Viper Venom, or isolated from plasma and similarly converted to Factor Xa can be converted to form a usable pharmaceutical by extending its half-life in serum. This can be accomplished by acylation of the serine at the active site which provides a slow release form of the active factor, also referred to herein as a "transiently inactivated" blood factor. Transient inactivation, via acylation or other means, of the other blood factors described in this invention confers similar slow-release features.

Thus, in certain embodiments, the invention is directed to Factor Xa wherein the serine residue at position 185 of the heavy chain is acylated with an agent which permits its appropriately timed conversion to active Factor Xa. Other aspects of the invention include pharmaceutical compositions for the treatment of hemophilia containing acylated Factor Xa, Factor IXa, and Factor VIIa of this invention and to methods to treat hemophilia using these compositions.

The transiently inactivated blood factors of this invention, their derivatives, or their antibodies are formulated into physiologically acceptable vehicles, especially for therapeutic, imaging and other diagnostic use. Such vehicles include sustained-release formulations. A composition is also provided comprising a transiently inactivated blood factor and a pharmaceutically acceptable carrier.

BRIEF DESCRIPTION OF THE DRAWINGS

FIG. 4 shows the cDNA sequence encoding Factor X.

MODES OF CARRYING OUT THE INVENTION

Figure 1:
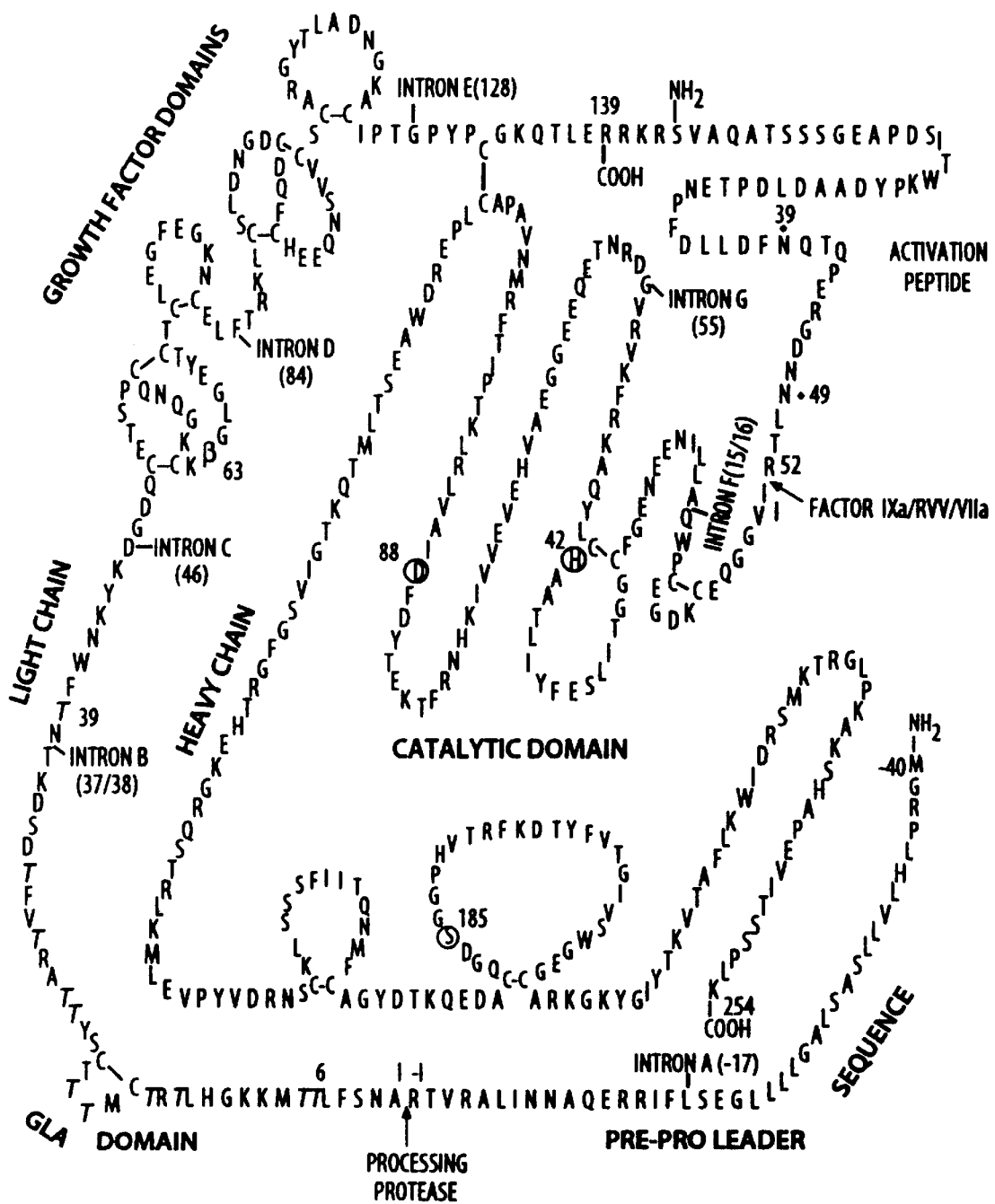
FIG. 1 shows the structure of human Factor X and its relevant cleavage sites as described in the prior art.

In general, one aspect of the invention encompasses the therapeutically useful two-chain polypeptide, designated Factor Xai herein, and the single-chain precursors of this two-chain protein. These peptides are about 80% homologous, preferably about 90% homologous to the amino acid sequences shown at positions 1–139 (light chain)

and 1–254 (heavy chain) in FIG. 1. It should be noted that in FIG. 1, the pre-pro leader sequence is numbered −40 through −1, prior to the numbering beginning at the N-terminus of the light chain. The light chain is numbered 1–139. The intervening tripeptide RKR, which, in mature Factor X, is deleted, is not numbered. The activation peptide beginning subsequent to this intervening tripeptide is numbered 1–52; the isoleucine referred to hereinbelow as "position 53" of the activation peptide is, in fact, the first amino acid of the heavy chain in the activated form. This restarts the numbering shown in the figure, and the heavy chain is numbered 1–254.

The embodiments of the two-chain peptide, Factor Xai, are effective in forming the prothrombinase complex, as determined by their ability to inhibit (or compete with) the formation of the native prothrombinase complex involving Factor Xa. Their ability to inhibit prothrombinase complex formation can be determined conveniently by the method of Krishnaswamy, S., *J Biol Chem* (1988) 263:3823–3834, cited above. However, when incorporated into the prothrombinase complex, the complex fails to show its proteolytic activity, as determined by the method of van Dieijen, G., et al., *J Biol Chem* (1981) 256:3433 or of Skogen, W. F. et al., *J Biol Chem* (1984) 256:2306. These Factor Xai proteins may or may not be immunoreactive with antibodies against native Factor Xa or against Factor X, including commercially available antibodies specific for human Factor X. The Factor Xai proteins are antithrombotic materials.

The invention is also directed to precursors of the foregoing inactive competitors with Factor Xa. One group of these precursors are novel modified forms of Factor X designated Factor X', wherein one or more of the residues at position 42, 88 or 185 of the heavy chain are converted to alternate amino acid residues, thus inactivating the proteolytic properties of the peptide. The modified forms of Factor X contain at a minimum the light chain sequence and the heavy chain sequence to which is attached the activation peptide. The intervening tripeptide (between the C-terminus of the light chain the N-terminus of the activation peptide) and the pre-pro leader sequence may or may not be present. Thus, the Factor X may either be a single-chain protein when the tripeptide is included) or a two-chain precursor of Factor Xa (when the tripeptide has been deleted).

Preferably, the alteration at the residues of the protease active site is either a deletion, or a conversion to a conservative, substituted amino acid so as to maintain the three-dimensional conformation of the two-chain protein. By "conservative" is meant a substitution which maintains the correct conformation, rather than a substitution which maintains the correct activity. Thus, the histidine residue at position 42 preferably replaced by phenylalanine; the aspartic acid at position 88 is preferably replaced by asparagine or glutamine, and the serine residue at position 185 is preferably replaced by alanine or glycine.

Figure 3:
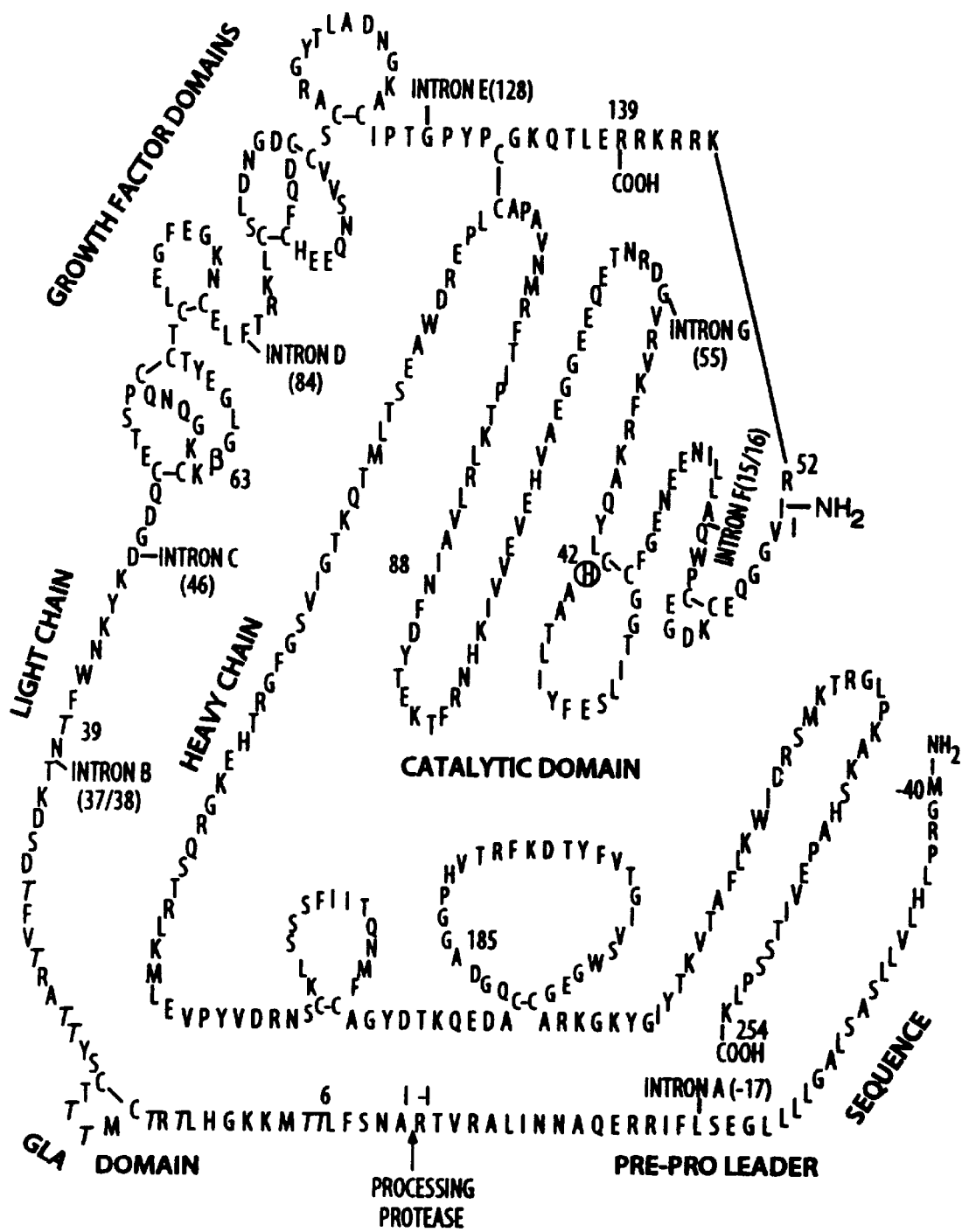
FIG. 3 shows one embodiment of Factor X'i.

Another group of precursors to the antithrombotic dimeric peptides of the invention is designated Factor X'i. In Factor X'i precursors, at least a substantial portion of the activation peptide, preferably the entire activation peptide, is deleted. The precursors to the two-chain form of Factor X'i, however, must retain a proteolytic cleavage site between the light and heavy chains. Therefore, amino acids subject to endogenous proteolysis are conveniently included in a single-chain precursor form which extends the carboxy terminus of the light chain by virtue of the cleavage site to the N-terminus of the heavy chain. A typical embodiment of the single-chain precursor (including the pre-pro leader) to the two-chain Factor X'i, which will now automatically be activated by virtue of the absence of the activation peptide sequence (thus, becoming a Factor Xai) is shown in FIG. 3. In this embodiment, the hexapeptide sequence RKRRKR connects the C-terminus of the light chain directly to the isoleucine residue at the N-terminus of the heavy chain. Cleavage of this single-chain Factor X'i results in X'ai.

Figure 2:
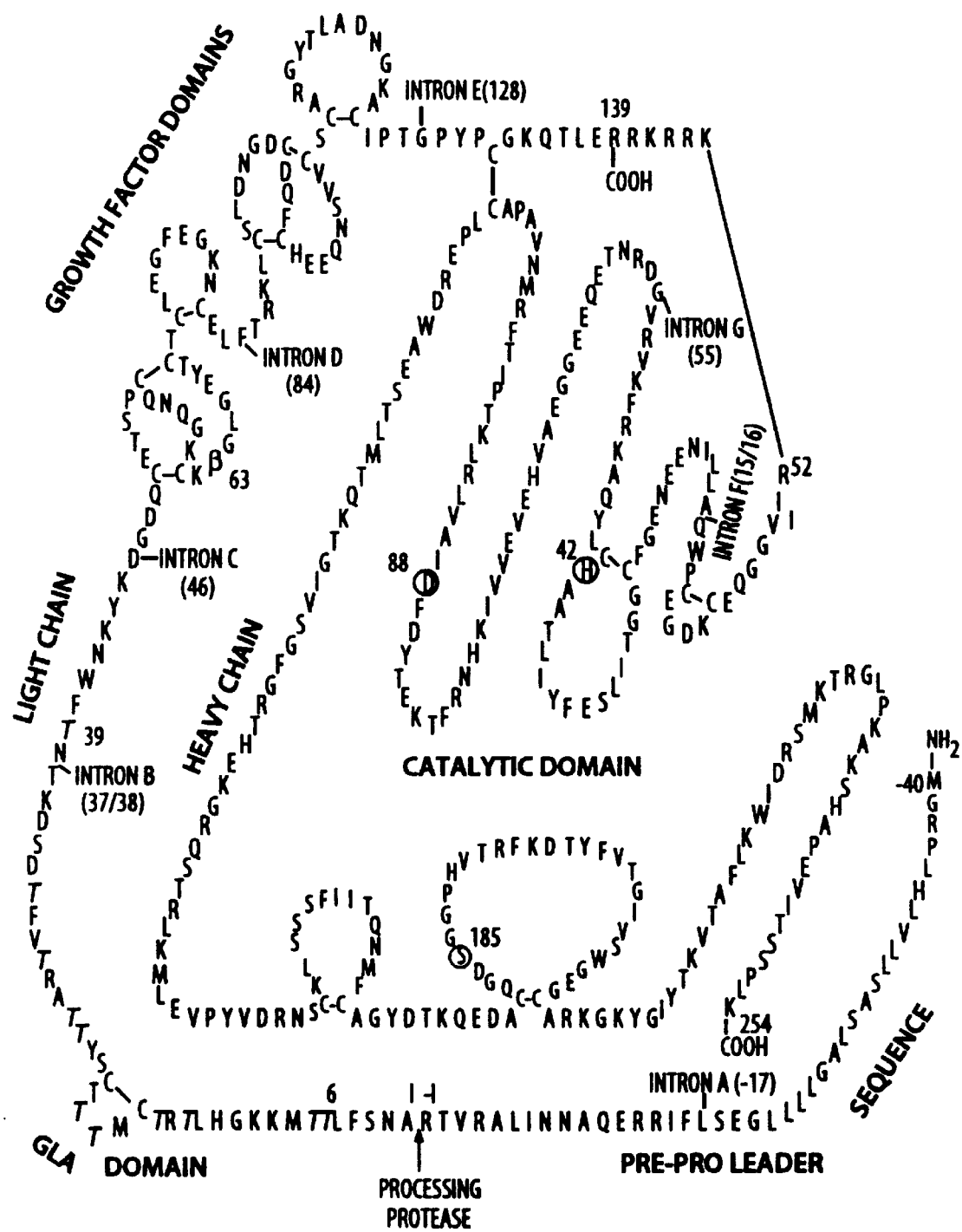
FIG. 2 shows the structure of one embodiment of a single-chain Factor X' which is a precursor to yield a two-chain cleavage product that will participate in prothrombinase complex formation. The form shown in this figure will produce a two-chain peptide which retains proteolytic activity in the complex; a modified form, as described below, is catalytically inactive.

In constructing such modified X'i type precursors, a hydrophobic amino acid must be retained at the N-terminus of the heavy chain (natively isoleucine). See, for example, Dayhoff, M. O., "Atlas of Protein Sequence and Structure" (1972) 5:89–99 (Biomed. Res. Foundation, Wash. D.C.) and Greer, J., *J. Molec. Biol.* (1981) 153:1043–1053. It is evident that the single-chain Factor X' precursors are also novel and, when cleaved by proteolysis, yield Factor Xa, the normal enzymatically-active form of the dimeric protein. This corresponding construction is shown in FIG. 2.

Thus, when the single-chain precursors of either Factor Xa or Factor Xai are produced recombinantly in suitable host cells, the endogenous enzymes of the host cell may (1) cleave the single-chain precursor Factor X or X' to a two-chain form and, in the case of single-chain Factor X or X', further activate the factor by cleavage of the activation peptide; in the case of Factor X' single-chain precursors, there is no activation peptide present, so the single-chain precursor will automatically be activated when cleaved into a dimeric peptide. For Factor X precursors, the double-chain form containing the activation peptide may also be cleaved in vitro using a suitable protease, such as the Factor X activator of Russell's viper venom. Either Factor Xa or Factor Xai will be obtained depending on whether the active site has been inactivated by alteration at the appropriate codons as further described hereinbelow.

To summarize the terminology used in this application, the following glossary may be useful:

"Factor X" refers to the native or recombinantly produced single- or two-chain Factor X sequence, essentially as shown in FIG. 1, containing at a minimum the heavy chain to which is attached the activation peptide, at its N-terminus, and the light chain. These may or may not be linked through a cleavage sequence as indicated in the figure.

"Factor IX", "Factor VII" and "activated Protein C" refer to the respective native or recombinantly produced protein sequence as commonly known.

"Blood factor" refers to blood coagulation factors generally, and preferably to a group of blood factors including Factor X, Factor VII, Factor IX, and Protein C, in their inactive, active, or inactivated active forms.

"rX" refers specifically to the recombinantly produced form of this factor.

"Factor Xi" refers to the recombinantly produced form of Factor X which lacks proteolytic activity by virtue of the modification of the act as described above. The designation "rXi" is also used for this protein.

"Factor Xa" refers to native or recombinantly produced, enzymatically active dimer containing light and heavy chain only. The activation peptide is not present in this complex.

"rXa" refers specifically to this complex when produced recombinantly.

"Factor Xai" refers to the modified form of Factor Xa which is activated in the sense that it combines to form the prothrombinase complex, but which has no serine protease activity by virtue of the modification of its active site. As this protein is produced only by recombinant methods, "IrXai" is also used to designate this complex.

"Factor X'" refers to a modified, single-chain form of Factor X which includes only the light chain, heavy chain, and an intermediate, specific proteolytic cleavage site, such as that shown in FIG. 2. This single-chain precursor may also contain the pre-pro sequence. As it is a result only of recombinant production, it is also designated "rX'." When cleaved by a protease so as to become activated, the products are indistinguishable from Factor Xa (or rXa) and, accordingly, this terminology is again used.

Similarly, "Factor X'i" refers to a modified form of Factor X' which has been inactivated at its catalytic site as described above. One form is shown in FIG. 3. Upon conversion to the two-chain form, as the activation peptide is not present in the precursor, the products are indistinguishable from Factor Xai or rXai.

"Acylated Factor Xa" or "AcXa", unless otherwise specified, refers to Factor Xa, whether produced recombinantly or not, wherein the serine residue at position 185 has been blocked with a substituent which provides the Factor Xa with a half-life in serum of at least 5–10 minutes, preferably more than 15 minutes, and which releases Factor Xa in active form over this time period. The half-life in serum can be measured directly in vivo using a suitably labeled form. However, it is preferable to assess the ability of the extended life AcXa to generate the active factor within the required time frame in vitro using as a criterion in vitro assays for which Xa is a catalyst. Under these conditions, suitable forms of AcXa for the invention include those which have a rate constant for hydrolysis in isotonic aqueous media at pH 7.4 and 37° C. such that a half-life of approximately 5 minutes to several hours is achieved. The half-life can be determined directly in vitro by measuring the rate of hydrolysis of the acylated Xa, if desired, using its ability to activate clotting, or the prothrombinase reaction as criteria for Xa formation.

The blood factors described in this invention are defined herein to be any isolated polypeptide sequence which possesses a biological property of the naturally occurring blood factor polypeptide comprising a commonly known polypeptide sequence, variants and homologues thereof, and mammalian or other animal analogues.

"Biological property" for the purposes herein means an in vivo effector or antigenic function or activity that is directly or indirectly performed by a blood factor (whether in its native or denatured conformation), or by any subsequence thereof. Effector functions include receptor binding, any enzyme activity or enzyme modulatory activity, any carrier binding activity, any hormonal activity, any activity in promoting or inhibiting adhesion of cells to an extracellular matrix or cell surface molecules, or any structural role. However, effector functions do not include antigenic functions, i.e. possession of an epitope or antigenic site that is capable of cross-reacting with antibodies raised against a naturally occurring blood factor polypeptide.

Ordinarily, the blood factors claimed herein will have an amino acid sequence having at least 75% amino acid sequence identity with a commonly known sequence, more preferably at least 80%, even more preferably at least 90%, and most preferably at least 95%. Identity or homology with respect to a commonly known blood factor sequence is defined herein as the percentage of amino acid residues in the candidate sequence that are identical with the known blood factor amino acid residues, after aligning the sequences and introducing gaps, if necessary, to achieve the maximum percent homology, and not considering any conservative substitutions as part of the sequence identity. None of N-terminal, C-terminal or internal extensions, deletions, or insertions into the blood factor sequence shall be construed as affecting homology.

Thus, the claimed transiently inactivated blood factor polypeptides and blood factors with extended plasma half-lives that are the subject of this invention include each blood factor sequence; fragments thereof having a consecutive sequence of at least 5, 10, 15, 20, 25, 30 or 40 amino acid residues from a commonly known blood factor sequence; amino acid sequence variants of a commonly known blood factor sequence wherein an amino acid residue has been inserted N- or C-terminal to, or within, the blood factor sequence or its fragment as defined above; amino acid sequence variants of the commonly known blood factor sequence or its fragment as defined above has been substituted by another residue. Blood factor polypeptides include those containing predetermined mutations by, e.g., site-directed or PCR mutagenesis, and other animal species of blood factor polypeptides such as rabbit, rat, porcine, non-human primate, equine, murine, and ovine blood factors, and alleles or other naturally occurring variants of the foregoing and human sequences; derivatives of the commonly known blood factor or its fragments as defined above wherein the blood factor or its fragments have been covalently modified by substitution, chemical, enzymatic, or other appropriate means with a moiety other than a naturally occurring amino acid (for example a detectable moiety such as an enzyme or radioisotope); glycosylation variants of the blood factor (insertion of a glycosylation site or deletion of any glycosylation site by deletion, insertion or substitution of appropriate amino acid); and soluble forms of the blood factor. Such fragments and variants exclude any transiently inactivated blood factor polypeptide heretofore identified, including any known protein or polypeptide of any animal species, which is otherwise anticipatory under 35 U.S.C. 102 as well as polypeptides obvious over such known protein or polypeptide under 35 U.S.C. 103, including acylated thrombin, acylated tissue plasminogen factor, urokinase, and streptokinase.

Preparation of the Invention Peptides

The genomic organization and coding sequence for human Factor X are known and the cDNA has been retrieved and sequenced (Leytus, S. P., et al., *Proc Natl Acad Sci USA* (1984) 81:3699; Kaul, R. K., et al., *Gene* 1(1986) 41:311–314). The complete Factor X cDNA sequence is shown in FIG. 4. Full length sequences for other blood factors such as thrombin, Factors IXa and VIIa, and activated Protein C are well known in the field. Throughout this specification, techniques described in relation to Factor X-related polypeptides are fully applicable to the other blood factors claimed in this invention, and are provided for exemplary purposes only.

Full-length Factor X cDNA inserts are subcloned into M13mp18 or M13mp19 vectors for site-directed mutagenesis. (The correct sequence encoding Factor X is verified by dideoxy sequencing.) Standard modification techniques are now readily available in the art, and thus the sequence encoding Factor X is modified to obtain the DNA-encoding Factor X', Factor Xi, and Factor X'i.

The modified coding sequences for Factor X', Factor Xi, Factor X'i and the other claimed blood factors are then ligated into suitable expression vectors for recombinant production of the polypeptides. In the expression vectors, the prepro leader sequence is preferably retained for expression in compatible host cells such as mammalian hosts. If bacterial or yeast expression is desired, it may be desirable to substitute a compatible leader sequence, such as the penicillinase sequence in bacteria, or the alpha-factor sequence in yeast. Alternatively, an ATG start codon may be directly placed before amino acid 1 of the light chain-encoding sequence to produce an intracellular protein.

The choice of host and expression control system is governed by the nature of the desired result. If endogenous activation by proteolytic cleavage is desired, mammalian systems may be preferable. However, production in microorganisms which provide simplicity of culturing is not precluded, provided an in vitro system for carboxylation to produce the required carboxy glutamyl residue is employed, or the microorganism or other host natively lacking this posttranslational processing system is transformed to provide it. A wide variety of expression systems for recombinant DNA sequences is known in the art.

The modified DNA encoding Factor X', Factor Xi, Factor X'i or other blood factor is preferably provided with linkers for ligation into cloning and expression vectors. Techniques for preparation of such vectors are well understood in the art. The DNA encoding the desired blood factor is ligated in operable linkage with control sequences, including promoters, upstream enhancers, termination sequences, and so forth, depending on the nature of the intended recombinant host cells. Technology is currently available for expression of heterologous genes in a variety of hosts, including prokaryotic hosts and various eucaryotes, including yeast, mammalian or avian or insect cells, and plant cells. The choice of control sequences and markers in the expression vectors is selected appropriately to these hosts.

For example, in prokaryotic hosts, various promoters, including inducible promoters such as promoter and lambda phage $P_L$ promoter can be employed. Hybrid promoters such as the tac promoter, which contains the trp polymerase binding region in combination with the lac operator, can be used. Suitable markers are generally those related to antibiotic resistance. On the other hand, in mammalian cell cultures, commonly used promoters are virally derived, such as the early and late SV40 promoters and adenovirus promoters. Mammalian regulatable promoters, such as the metallothionein-II promoter may also be used. The metallothionein-II promoter is regulated by glucocorticoids or heavy metals. These promoter systems are compatible with typical mammalian hosts, the most commonly used of which is Chinese hamster ovary (CHO) cells.

Another commonly employed system is the baculovirus expression system compatible with insect cells. Plant cells, used in conjunction with, for example, the nopaline synthetase promoter, and yeast cells, used in conjunction with promoters associated with enzymes important in the glycolytic pathway, can also be employed. A number of suitable expression systems can be found in appropriate chapters in "Current Protocols in Molecular Biology," Ausubel, F. M., et al., eds., published by Wiley Interscience, latest edition.

Certain preferred aspects of this invention relate to transiently inactivated blood factors, such as Factors VIIa, IXa, Xa, and activated Protein C. Transient inactivation may be accomplished by a variety of methods, including binding of an antibody/antibody fragment to the active region, binding of moiety which blocks sterically the proteolytic or other active domain, or incorporation of a chemical moiety which blocks the active blood factor domain and gradually is released from the blood factor. Particularly preferred embodiments of this invention are blood factor polypeptides which are transiently inactivated by being acylated.

For purposes of this application, reversible inactivation of the blood factors of this invention may be accomplished using benzamidines, which are good reversible inhibitors of trypsin-like enzymes. The cationic amidino group of the inhibitor interacts with an enzyme carboxylate located at the bottom of the S1 subsite. A wide variety of substituted benzamidines have been investigated as inhibitors of thrombin and plasmin and are suitable for practice of this invention (see e.g., Andrews J M, Roman D P, Bing D M and Corey M. J Med Chem 21, 1202–1207, 1978). Extensive studies have been reported on compounds containing two benzamidine moieties, which are also desirable for the practice of this invention (see e.g., Tidwell R R, Webster W P, Shaver S R and Geratz J D. Thrombosis Research, 19, 339–349, 1980). Also useful for this invention is 1,2-bis(5-amidino 2-benzofuranyl) ethane, which is known to inhibit factor Xa with a Ki of 570 nM.

Also suitable for transient inactivation of proteins according to this invention are Kunitz inhibitors (a class of widely studied protease inhibitors). Bovine pancreatic trypsin inhibitor (aprotinin) and tissue factor pathway inhibitor (also known as LACI) belong to this class. Dissociation constants ($T_{1/2}$) can range from 17 weeks to 11 seconds (Gebhard W, Tschesche H and Fritz H. Proteinase Inhibitors, Elsevier, 1986). Aprotinin competitively inhibits factor VIIa with a Ki of 3 uM (Chabbat J, Porte P, Tellier M and Steinbuch M. Thrombosis Research, 71, 205–215, 1993).

The acylated polypeptides of this invention, such as AcXa, AcIXa, AcVIIa, and Acylated activated Protein C, are prepared by standard acylation reaction of the corresponding blood factor, whether recombinantly produced or isolated from plasma, according to procedures analogous to those set forth, for example, or referenced in Cassels, R. et al. *Biochem J* (1987) 247:395–400 or U.S. Pat. No. 4,337,244 cited above.

In certain embodiments of this invention, the blood factor is treated with a three to ten-fold molar excess of an acylating agent in a neutral pH buffer at room temperature. Catalytic activity is followed over a time course of approximately one to sixty, and preferably for ten to thirty minutes to assure the desired level of inactivation of protein. The reagent is preferable prepared as a 0.1M solution in DMSO and added to the protein at pH 7.5. Blocked protein is subjected to gel filtration (preferably on a Sephadex G-25 column) at pH 5.0 to remove excess reagent. Protein may be stored at pH 5.0 at −70° C.–80° C. prior to further use.

Suitable active site acyl groups for use in this invention include benzoyl, p or o methyl (toluoyl), p or o methoxy (p is a more preferred anisoyl), p or o fluoro benzoyl, Dimethyl acryloyl (3,3 or 3,4), Difluoro compounds, $CH_3CO$ benzene (acetyl gp), $CH_3CONH$ benzene (acetanilide), p or o ethoxy (or other alkyl groups), and guanidino benzoyl.

Suitable esters for use in this invention include the 4-toluoyl ester, the 3,3-dimethyl acrylyl ester, cyclohexylidineacetyl ester, the cyclohex-1-enecarbonyl ester, the 1-methylcyclohexylidineacetyl ester, the 4-aminobenzoyl ester, the guanidinobenzoyl ester, the 4-anisoyl ester, the 4-N, N dimethylaminobenzoyl ester, and the PDAEB (4-N-(2-N'-(3-(2-pyridyldithio)-propenyl)amino-ethyl) aminobenzoyl ester. In general, the acylating agent will be the activated form of a non-toxic acid which provides a saturated, unsaturated or aromatic 5- or 6-carbon ring to which a carboxyl is substituted. The ring may contain further substitutions, such as amino, alkoxy, alkyl, additional ring systems, or any other non-interfering non-toxic substituent. For Factor X and other blood factors with a catalytically active serine domain, any compound capable of acylating the serine hydroxyl group or otherwise blocking the serine catalytic domain in a reversible manner is suitable for synthesis of the acylated blood factor. As described in U.S. Pat. No. 4,337,244, in general, either direct or inverse acylating agents can be used. For direct acylating agents, the acylating moiety is itself attracted to the catalytic site of the Factor Xa or other blood factor; in the inverse acylating approach, the leaving group is thus attracted. The acylated form of the blood factor is then purified from the reaction mixture using standard purification techniques, including dialysis, chromatography, selective extraction, and the like.

Potent acylating agents such as 3-alkoxy 4-chloroisocoumarins have been reported for a variety of serine proteases (Harper J W and Powers J C. JACS 106, 7618–7619, 1984. Harper J W and Powers J C. Biochemistry 24, 7200–7213, 1985) and are suitable for use in accordance with this application. The stability of the acyl enzymes are dependent on the alkoxy groups, small groups give transiently stable ($T_{1/2}<2$ h) acyl enzymes.

The compounds of the invention which serve as acylated blood factor diagnostics and/or pharmaceuticals must have an appropriate deacylation rate which assures an appropriate clearance time in vivo. The acylated proteins reactivate in a time, temperature and pH dependent manner. Typically, deacylation is faster at 37° C. than at room temperature, and is faster at pH 8.0 than at pH 7.5. The deacylation rate can be measured as having a half life of at least 5 minutes in vitro in buffer using prothrombinase and/or clotting assays. Deacylation can be measured directly as described by Smith, R. A. G., et al., "Progress in Fibrinolysis" (1985) Vol. VII, pp. 227–231 (Churchill Livingstone). Prothrombinase and clotting assays are described by Wolf, D. L., et al. *J Biol Chem* (1991) 266:13726.

In certain preferred embodiments, deacylation of acyl factors Xa and aPC is carried out by incubation in a solution of appropriate pH and assaying aliquots in an amidolytic or clotting assay. The relative activity is calculated as a percentage of equivalent amount of active factor Xa or aPC carried through the same incubations. The preferred assay for acyl factor VIIa involves multiple steps. The acyl enzyme is incubated in the appropriate buffer at a protein concentration of 160 nM. At each time point an aliquot is diluted to 0.16 nM and incubated with lipidated tissue factor (0.25 nM) for 1 min at room temperature. The factor VIIa/Tissue Factor mixture is then used for activation of factor X and resulting factor Xa assayed in an amidolytic assay.

Covalent modifications of the preferably acylated blood factors are included within the scope of this invention. Both native blood factor and amino acid sequence variants of the blood factor optionally are covalently modified. One type of covalent modification included within the scope of this invention is a blood polypeptide fragment. Blood factor fragments having up to about 40 amino acid residues are conveniently prepared by chemical synthesis, or by enzymatic or chemical cleavage of the full-length blood factor polypeptide or blood factor variant polypeptide. Other types of covalent modifications of the blood factor or fragments thereof are introduced into the molecule by reacting targeted amino acid residues of the blood factor or fragments thereof with an organic derivatizing agent that is capable of reacting with selected side chains or the N- or C-terminal residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-b-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the transiently inactivated blood factor to a water-insoluble support matrix or surface for use in the method for purifying anti-blood factor antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group.

The transiently inactivated blood factor of this invention optionally is fused with a heterologous polypeptide. The heterologous polypeptide optionally is an anchor sequence such as that found in the decay accelerating system (DAF); a toxin such as ricin, pseudomonas exotoxin, gelonin, or other polypeptide that will result in target cell death. These heterologous polypeptides are covalently coupled to the blood factor polypeptide through side chains or through the terminal residues. Similarly, other molecules toxic or inhibitory to a target mammalian cell (e.g. cancer cell) are coupled to the blood factor such as tricothecenes, or antisense DNA that blocks expression of critical genes.

The transiently inactivated blood factor of this invention is covalently modified by altering its native glycosylation pattern. One or more carbohydrate substituents in these embodiments are modified by adding, removing or varying the monosaccharide components at a given site, or by modifying residues in the blood factor as glycosylation sites are added or deleted.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Glycosylation sites are added to the blood factor of this invention by altering its amino acid sequence to contain one or more of the above-described tri-peptide sequences (for N-linked glycosylation sites). The alteration may also be made by the addition of, or substitution by, one or more serine or threonine residues to the blood factor (for O-linked glycosylation sites). For ease, the blood factor is preferably altered through changes at the DNA level, particularly by mutating the DNA encoding the blood factor at preselected bases such that codons are generated that will translate into the desired amino acids.

Chemical or enzymatic coupling of glycosides to the blood factor increases the number of carbohydrate substituents. These procedures are advantageous in that they do not require production of the polypeptide in a host cell that is capable of N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, published Sep. 11, 1987, and in Aplin and Wriston (*CRC Crit. Rev. Biochem., pp.* 259–306 [1981]).

Carbohydrate moieties present on the blood factor also are removed chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al. (*Arch. Biochem. Biophys.,* 259:52 [1987]) and by Edge et al. (*Anal. Biochem.,* 118:131 [1981]). Carbohydrate moieties are removed from the blood factor by a variety of endo- and exo-glycosidases as described by Thotakura et al. (*Meth. Enzymol.,* 138:350 [1987]).

Glycosylation also is suppressed by tunicamycin as described by Duskin et al. (*J. Biol. Chem.,* 257:3105 [1982]). Tunicamycin blocks the formation of protein-N-glycoside linkages.

The blood factor also is modified by linking it to various nonproteinaceous polymers, e.g., polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

One preferred way to increase the in vivo circulating half life of a circulating blood factor is to conjugate it to a polymer that confers extended half-life, such as polyethylene glycol (PEG). (Maxfield, et al, Polymer 16,505–509 [1975]; Bailey, F. E., et al, in Nonionic Surfactants [Schick, M. J., ed.] pp. 794–821, 1967); (Abuchowski, A. et al., J. Biol. Chem. 252, 3582–3586, 1977; Abuchowski, A. et al, *Cancer Biochem. Biophys.* 7, 175–186, 1984); (Katre, N. V. et al., *Proc. Natl. Acad. Sci.,* 84, 1487–1491, 1987; Goodson, R. et al. *Bio Technology,* 8, 343–346, 1990). Conjugation to PEG also has been reported to have reduced immunogenicity and toxicity (Abuchowski, A. et al., *J. Biol. Chem.,* 252, 3578–3581, 1977).

The blood factor also is entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, phospholipid vesicles, albumin microspheres, microemulsions, nano-particles and nanocapsules), or in macroemulsions. Such techniques are disclosed in *Remington's Pharmaceutical Sciences,* 16th edition, Osol, A., Ed., (1980).

The transiently inactivated blood factors of this invention is also useful in generating antibodies, as standards in assays for the blood factor (e.g., by labeling the blood factor for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Those skilled in the art will be capable of screening variants in order to select the optimal variant for the purpose intended. For example, a change in the immunological character of the transiently inactivated blood factor, such as a change in affinity for a given antibody or for the factor's natural receptor or ligand, is measured by a competitive-type immunoassay using a standard or control such as a native blood factor. Other potential modifications of protein or polypeptide properties such as redox or thermal stability, hydrophobicity, susceptibility to proteolytic degradation, stability in recombinant cell culture or in plasma, or the tendency to aggregate with carriers or into multimers are assayed by methods well known in the art.

Administration and Use

The Factor Xai peptides of the invention are prothrombinase inhibitors and are thus useful in procedures complicated by thrombosis and in conditions whose pathogenesis involves thrombin generation. These conditions include those involving arterial thrombosis, such as unstable (i.e., rest) angina and abrupt vessel closure during vascular interventions including coronary and peripheral angioplasty and atherectomy, and during and after vascular bypass procedures (peripheral and coronary), reocclusion after thrombolytic therapy for myocardial infarction, thrombotic stroke (stroke in evolution), and thrombosis due to vasculitis (Kawasaki's disease). Also included are conditions involving venous thrombosis, such as deep venous thrombosis of the lower extremities, pulmonary embolism, renal vein, hepatic vein, inferior vena cava thrombosis, and cavernous sinus thrombosis. Other target conditions are those involving diffuse activation of the coagulation system, such as sepsis with disseminated intravascular coagulation, disseminated intravascular coagulation in other settings, thrombotic thrombocytopenic purpura, and rare conditions of unknown etiology (Lupus anticoagulant).

The Factor Xai of the invention is also useful as an anticoagulant and anti-inflammatory for cardiopulmonary bypass, in harvesting organs, in preparation of blood products or samples and in transport and implantation of organs and associated treatment of the recipient. The Factor Xai, in a slow release form, is especially useful in indwelling intravascular devices (i.v.s, catheters, grafts, patches).

Thrombosis also plays. a role in restenosis following vascular interventions such as angioplasty, atherectomy, or endarterectomy by directly or indirectly causing smooth muscle cell proliferation, and the Factor Xai of the invention is also useful in treating this condition.

Adult respiratory distress syndrome (ARDS) is thought to be an "endotoxin" disease in which a prothrombotic endothelium is likely to exist, with inflammatory and proliferative components; Factor Xai is also useful in treatment of ARDS.

The transiently inactivated activated Protein C polypeptides of this invention are useful as antithrombotics. The transiently inactivated Factors IXa, Xa, and VIIa of this invention are useful hemostatic factors, particularly for the treatment of hemophilia as replacement or bypass factors. The modified blood factors of this invention, modified to extend their half-life in vivo, are useful in treating hemophilia whether the origin of the hemophilia resides in the Factor X, IX, or VII gene, or the more widespread types, hemophilias A and B.

Therapeutic formulations of the blood factors of this invention, or of a blood factor antibody are prepared for storage by mixing the blood factor polypeptide or antibody having the desired degree of purity with optional physiologically acceptable carriers, excipients, or stabilizers (*Remington's Pharmaceutical Sciences,* supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as Tween, Pluronics or polyethylene glycol (PEG).

The blood factor or blood factor antibody to be used for in vivo administration must be sterile. This is readily accomplished by filtration through sterile filtration membranes, and may be performed prior to or following lyophilization and reconstitution. The blood factor or antibody to the blood factor ordinarily will be stored in lyophilized form or in solution.

Therapeutic blood factor compositions, or blood-factor specific antibody compositions generally are placed into a container having a sterile access port, for example, an intravenous solution bag or vial having a stopper pierceable by a hypodermic injection needle.

The blood factor, its antibody or variant may be optionally combined with or administered in concert with other agents known for use in the treatment of particular coagulation disorders, such as thrombolytics (including tPA, streptokinase and urokinase), heparin, aspirin, Hirudin, Hirulog. When the blood factor is used to stimulate coagulation, it may be combined with or administered in concert with other compositions that stimulate coagulation.

The route of the blood factor or blood factor antibody administration is in accord with known methods, e.g., injection or infusion by intravenous, intraperitoneal, intracerebral, intramuscular, intraocular, intraarterial, or intralesional routes, or by sustained release systems as noted below. The blood factor is preferably administered continuously by infusion or by bolus injection. Blood factor antibody is administered in the same fashion, or by administration into the blood stream or lymph.

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogels [e.g., poly(2-hydroxyethyl-methacrylate) as described by Langer et al., *J. Biomed. Mater. Res.,* 15: 167–277 [1981] and Langer, *Chem. Tech.,* 12: 98–105 [1982] or poly (vinylalcohol)], polylactides (U.S. Pat. No. 3,773,919, EP 58,481), copolymers of L-glutamic acid and gamma ethyl-L-glutamate (Sidman et al., *Biopolymers,* 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133, 988). While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release blood factor or antibody compositions also include liposomally entrapped blood factor or antibody. Liposomes containing the claimed blood factor or antibody are prepared by methods known per se: DE 3,218,121; Epstein et al., *Proc. Natl. Acad. Sci. USA,* 82:3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal blood factor therapy. Liposomes with enhanced circulation time are disclosed in U.S. Pat. No. 5,013,556. Additionally, Giles, A. R., et al. *Brit J Hematol* (1988) 69:491–497 describe the formulation of Factor Xa in phosphatidylcholine-phosphatidylserine vesicles.

Another use of the present invention comprises incorporating the blood factor polypeptide or antibody into formed articles. Examples of such articles include vascular stents, grafts, surgical tubing, etc. Such articles can be used in modulating cellular growth and development. In addition, cell growth and division, and tumor invasion may be modulated with these articles.

An effective amount of the blood factor or antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 mg/kg to up to 100 mg per patient, and more preferably of 1–50 mg per patient per continuous injected dose, depending on the factors mentioned above. Typically, the clinician will administer the blood factor or antibody until a dosage is reached that achieves the desired effect. The progress of this therapy is easily monitored by conventional assays.

Certain aspects of this invention are directed to antibodies to the blood factors. The antibodies of this invention are obtained by routine screening. Polyclonal antibodies to the blood factor generally are raised in animals by multiple subcutaneous (sc) or intraperitoneal (ip) injections of the blood factor and an adjuvant. It may be useful to conjugate the blood factor or blood factor fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The route and schedule of immunizing an animal or removing and culturing antibody-producing cells are generally in keeping with established and conventional techniques for antibody stimulation and production. While mice are frequently immunized, it is contemplated that any mammalian subject including human subjects or antibody-producing cells obtained therefrom can be immunized to generate antibody producing cells.

Subjects are typically immunized against the blood factor or its immunogenic conjugates or derivatives by combining 1 mg or 1 mg of blood factor immunogen (for rabbits or mice, respectively) with 3 volumes of Freund's complete adjuvant and injecting the solution intradermally at multiple sites. One month later the subjects are boosted with ⅕ to ¹⁄₁₀ the original amount of immunogen in Freund's complete adjuvant (or other suitable adjuvant) by subcutaneous injection at multiple sites. 7 to 14 days later animals are bled and the serum is assayed for anti-blood factor antibody titer. Subjects are boosted until the titer plateaus. Preferably, the subject is boosted with a conjugate of the same blood factor, but conjugated to a different protein and/or through a different cross-linking agent. Conjugates also can be made in recombinant cell culture as protein fusions. Also, aggregating agents such as alum are used to enhance the immune response.

After immunization, monoclonal antibodies are prepared by recovering immune lymphoid cells—typically spleen cells or lymphocytes from lymph node tissue—from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.* 6:511 (1976) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

Hybridoma cell lines producing anti-blood factor are identified by screening the culture supernatants for antibody which binds to the blood factor. This is routinely accomplished by conventional immunoassays using blood factor preparations or by FACS using cell-bound blood factor and labeled candidate antibody.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of the blood factor in test samples.

While mouse monoclonal antibodies routinely are used, the invention is not so limited; in fact, human antibodies may be used and may prove to be preferable. Such antibodies can be obtained by using human hybridomas (Cote et al., *Monoclonal Antibodies and Cancer Therapy*, Alan R. Liss, p. 77 (1985)). Chimeric antibodies, Cabilly et al., U.S. Pat. No. 4,816,567, (Morrison et al., *Proc. Natl. Acad. Sci.,* 81:6851 (1984); Neuberger et al., *Nature* 312:604 (1984); Takeda et al., *Nature* 314:452 (1985)) containing a murine anti-blood factor variable region and a human constant region of appropriate biological activity (such as ability to activate human complement and mediate ADCC) are within the scope of this invention, as are humanized anti-blood factor antibodies produced by conventional CDR-grafting methods.

Techniques for creating recombinant DNA versions of the antigen-binding regions of antibody molecules (known as Fab or variable regions fragments) which bypass the generation of monoclonal antibodies are encompassed within the practice of this invention. One extracts antibody-specific messenger RNA molecules from immune system cells taken from an immunized subject, transcribes these into complementary DNA (cDNA), and clones the cDNA into a bacterial expression system and selects for the desired binding characteristic. The Scripps/Stratagene method uses a bacteriophage lambda vector system containing a leader sequence that causes the expressed Fab protein to migrate to the periplasmic space (between the bacterial cell membrane and the cell wall) or to be secreted. One can rapidly generate and screen great numbers of functional Fab fragments to identify those which bind the blood factor with the desired characteristics.

Antibodies capable of specifically binding to the proteolytically active domains of the blood factors are of particular interest. These antibodies are identified by methods that are conventional per se. For example, a bank of candidate antibodies capable of binding to the blood factor are obtained by the above methods using immunization with the full length polypeptide. These can then be subdivided by their ability to bind to the various blood factor polypeptide domains using conventional mapping techniques. Less preferably, antibodies specific for a predetermined domain are initially raised by immunizing the subject with a polypeptide comprising substantially only the domain in question, e.g. Factor X with an active serine protease domain. These antibodies may require routine mapping if binding to a particular epitope is desired.

Antibodies that are capable of binding to proteolytic processing sites are of particular interest in the practice of this invention. They are produced either by immunizing with a blood factor fragment that includes the processing site or with intact blood factor and then screening for the ability to block or inhibit proteolytic processing of the blood factor into the activated blood factor form. These antibodies are useful for suppressing the release of the activated blood factor and therefore are promising for use in preventing the release of activated blood factor and stimulation of its pro- or anti-coagulant activities. Many such proteolytically active and proteolytic processing sites have been mapped and are commonly known for the blood factors discussed herein. As described above, the antibodies should have high specificity and affinity for the target sequence.

Isolated blood factors may be used in quantitative diagnostic assays as a standard or control against which samples containing unknown quantities of the blood factor may be compared.

Blood factor antibodies are useful in diagnostic assays for blood factor expression in specific cells or tissues. The antibodies are labeled in the same fashion as the blood factor described above and/or are immobilized on an insoluble matrix.

Blood factor antibodies also are useful for the affinity purification of the blood factor from recombinant cell culture or natural sources. Blood factor antibodies that do not detectably cross-react with other blood factors, or which react only with the inactive, activated or inactivated active form of a particular blood factor can be used to purify that blood factor free from other known ligands or other protein.

Suitable diagnostic assays for the blood factors of this invention and their antibodies are well known per se. Such assays include commonly known competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of the blood factor and for substances that bind the blood factor, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for the blood factor of this invention or its antibodies all use one or more of the following reagents: labeled analyte analogue, immobilized analyte analogue, labeled binding partner, immobilized binding partner and steric conjugates. The labeled reagents also are known as "tracers."

The label used (and this is also useful to label blood factor encoding nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, technetium, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, b-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature,* 144: 945 (1962); David et al., *Biochemistry,* 13: 1014–1021 (1974); Pain et al., *J. Immunol. Methods,* 40:219–230 (1981); and Nygren, *J. Histochem. and Cytochem.,* 30:407–412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, N.Y, 1981), pp. 147–166. Such bonding methods are suitable for use with the blood factor or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde crosslinking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the blood factor or its immunologically active fragments are conjugated with a bifunctional organic bridge to an enzyme such as peroxidase. Conjugates are selected for use with anti-blood factor so that binding of the anti-blood factor antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of blood factor or blood factor antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-blood factor monoclonal antibody as one antibody and a polyclonal anti-blood factor antibody as the other is useful in testing samples for blood factor activity.

The foregoing are merely exemplary diagnostic assays for blood factors and blood factor antibodies. Other methods now or hereafter developed for the determination of these analytes are included within the scope hereof, including the bioassays described above.

All references cited in this specification are expressly incorporated by reference. The following examples are intended to illustrate, but not limit the invention.

EXAMPLE 1

Construction of DNA Encoding Catalytically Inactive Forms of Recombinant Human Factor X (rXi)

A full length cDNA clone for human Factor X was obtained from Dr. W. R. Church, University of Vermont (FIG. 4). This cDNA encodes the amino acid sequence of FIG. 1 or an allelic variant. This human Factor X cDNA was cloned into EcoRI site of vector pBSII (Stratagene) to obtain pBSX. The HindIII-XbaI fragment of pBSX comprising the entire Factor X coding region was subcloned into the Hind III-XbaI site of vector M13mplg (Mpl9X). Oligonucleotide site-directed mutagenesis was then performed as described by Kunkel, T. A., et al., *Methods in Enzymol* (1987) 154:367.

The following forms were produced:

The oligomer TGC CGA GGG GAC GCC GGG GGC CCG CAC was used to convert serine ($S_{185}$) at position 185aa on the Factor X heavy chain to alanine ($A_{185}$) to obtain rXi$A_{185}$.

The oligomer ACC TAT GAC TTC AAC ATC GCC GTG CTC was used to convert aspartic acid ($D_{88}$) at position 88aa on the Factor X heavy chain to asparagine ($N_{88}$) to obtain the gene encoding rXi$N_{88}$.

Both oligomers were used to obtain the gene encoding rXi$N_{88}A_{185}$. (See FIG. 1 for location of these sites). Verification of oligonucleotide-directed mutagenesis was accomplished by dideoxy sequencing.

EXAMPLE 2

Construction of DNA Encoding the Truncated Precursor of Human Factor Xa (rX')

The cDNA of human Factor X (Mpl9X) was converted to encode various truncated forms of human Factor Xa, collectively designated rX', by deletion of the activation peptide, by oligonucleotide site directed mutagenesis (Kunkel, T. A., et al., *Methods in Enzymol* (1987) 154:367). The following oligonucleotides employed with the corresponding amino acid changes are as follows:

rX'Δ0: ACC CTG GAA CGC AGG AAG AGG ATC GTG GGA GGC CAG GAA TGC, which aligned arginine (R142) following the C-terminus of the Factor X light chain with isoleucine ($I_{53}$) 53aa of the Factor X activation peptide (1aa of the heavy chain);

rX'Δ1: ACC CTG GAA CGC AGG AAG AGG AGA ATC GTG GGA GGC CAG GAA TGC, which aligned this $R_{142}$ with arginine ($R_{52}$) of the Factor X activation peptide;

rX'Δ2: ACC CTG GAA CGC AGG AAG AGG CGG AAA AGA ATC GTG GGA GGC CAG GAA TGC, which extended $R_{142}$ following the Factor X light chain by two amino acids arginine ($R_{143}$) and lysine ($K_{144}$) and aligned this terminus with $R_{52}$ of the Factor X activation peptide (FIG. 2);

rX'Δ3: ACC CTG GAA CGC AGG AAG AGG CCT AGG CCA TCT CGG AAA CGC AGG ATC GTG GGA GGC CAG GAA TGC, which extended $R_{142}$ following the Factor X light chain by seven amino acids, Proline ($P_{143}$) Arginine ($R_{144}$) Proline ($P_{145}$) Serine ($S_{146}$) Arginine ($R_{147}$) Lysine ($K_{148}$) Arginine ($R_{149}$) as described in Ehrlich, H. J., et al. *J Biol Chem* (1989) 264:14298, and aligned this terminus with $R_{52}$ of the Factor X activation peptides.

Verification of the oligonucleotide directed mutagenesis was accomplished by dideoxy sequencing.

As will be further described below, the precursor derived from rXI Δ2 was cleaved endogenously when recombinantly produced in CHO cells to obtain directly the activated form rXa. The precursor derived from rX'Δ0 was not cleaved endogenously in CHO cells when produced recombinantly. The precursor derived from rX'Δ1 or from rX'Δ3 was cleaved incompletely. The dimeric peptides derived from rX'Δ0, rX'Δ1 and rX'Δ3 were not active enzymatically.

EXAMPLE 3

Construction of DNA Encoding Catalytically Inactive Truncated Precursor (rX'i)

cDNA Factor X' constructs described in Example 2 were converted to encode the catalytically inactive forms of X' (rX'i) by oligonucleotide site-directed mutagenesis as described in Example 1. These constructs included rX'i(Δ2) $N_{88}$ (rX'i(Δ2)$N_{88}$) and rX'i(Δ2)$N_{88}A_{185}$, as shown in FIG. 3.

EXAMPLE 4

Expression of the Genes Encoding Precursor (rX and rX')

The expression vector pRC/CMV (Invitrogen) was modified by replacing the CMV promoter with the SRa promoter (Takabe, Y., et al., *Molec Cell Biol* (1988) 8:466). The ClaI-XbaI fragment, filled in by Klenow polymerase at the ClaI site which contained the SRa promoter was isolated from the expression vector pBJI (Lin, A., et al., *Science* (1990) 249:677 and available from M. Davis, Stanford University) and subcloned into the NruI-XbaI site of pRC/CMV creating expression vector pBN. The StuI fragment of pBN, comprising the SRa promoter, bovine growth hormone polyadenylation site and M13 origin or replication was subcloned into the StuI site of pSV2DHFR generating expression vector pBD. The Mp19 SmaI-EcoRV fragments of the precursor DNAs described in examples were subcloned into the Klenow polymerase filled-in XbaI site of pBN and pBD. The resulting expression vectors were transfected into CHO by lipofection (BRL). Selection for transfected clones was by either 1 mg/ml G418 Neomycin (Gibco) or 25 ng/ml Methotrexate (Sigma). Single clones were isolated by cloning cylinders, expanded and expression levels were determined on 24 hour serum free medium by a standard solid phase antibody capture assay (ELISA) as described by Harlow, E., and Lane, D., in *Antibodies* (1988), Cold Spring Harbor Laboratory, New York. The ELISA utilized a primary antibody of rabbit polyclonal antihuman Factor X (STAGO, American Diagnostics Inc.) and a rabbit-specific secondary antibody of peroxidase conjugated goat IgG.

Clones from constructs pBNX, pBNX'Δ0, pBNX'Δ1 pBNX'Δ2, and pBNX'Δ3 were expanded to confluence in T-7t tissue culture flasks in RPMI medium supplemented with 10% fetal bovine serum, Penicillin, Streptomycin, Glutamine and 10 μg/ml vitamin K, washed four times with serum free medium and incubated overnight with serum free medium.

Post-incubation the medium was harvested, centrifuged at 3000 rpm and 2 ml was precipitated with 10% Trichloracetic acid (TCA). The TCA pellet was washed three times with 100% Acetone, resuspended to 0.05 ml SDS-PAGE sample buffer or 0.05 m SDS-PAGE sample buffer with 1M β Mercaptoethanol. Duplicate 10 μl aliquots were electrophoresed on 12% SDS polyacrylamide gels and transferred to Immobilon filters (Millipore). Western blot analysis was performed with the primary human Factor X polyclonal rabbit sera (STAGO, American Diagnostics, Inc.) at a 1/4000 dilution in 1% nonfat dry milk, 0.1% NP40, 10 mM Tris-HCl pH 7.5, 150 mm NaCl. The secondary antibody was $^{125}I$ labeled Fab donkey antirabbit IgG (Amersham). Autoradiography was overnight at −70° C. with an intensifier screen.

The pattern of antibody reactivity showed that the expected products were produced. All five products, i.e., those derived from rX, rX'Δ0, rX'Δ1, rX'Δ2, and rX'Δ3 were positive in the above ELISA based on rabbit polyvalent human Factor X antisera. ELISAs were also performed with respect to mouse monoclonal antibodies Mab323, Mab743 and Mab325. Mab323 is specifically reactive with the activation peptide. Mab743 is reactive with either the activated or inactivated form of human Factor X. Mab325 is calcium ion dependent and directed to the light chain; this antibody reacts with the gammacarboxylated region.

Supernatants from cultures containing any of the five constructs gave positive ELISAs with Mab743 and Mab325; thus, posttranslational GLA processing is indicated in all cases. All of the rX' mutants failed to react with Mab323 confirming the absence of the activation peptide.

Figure 5A:
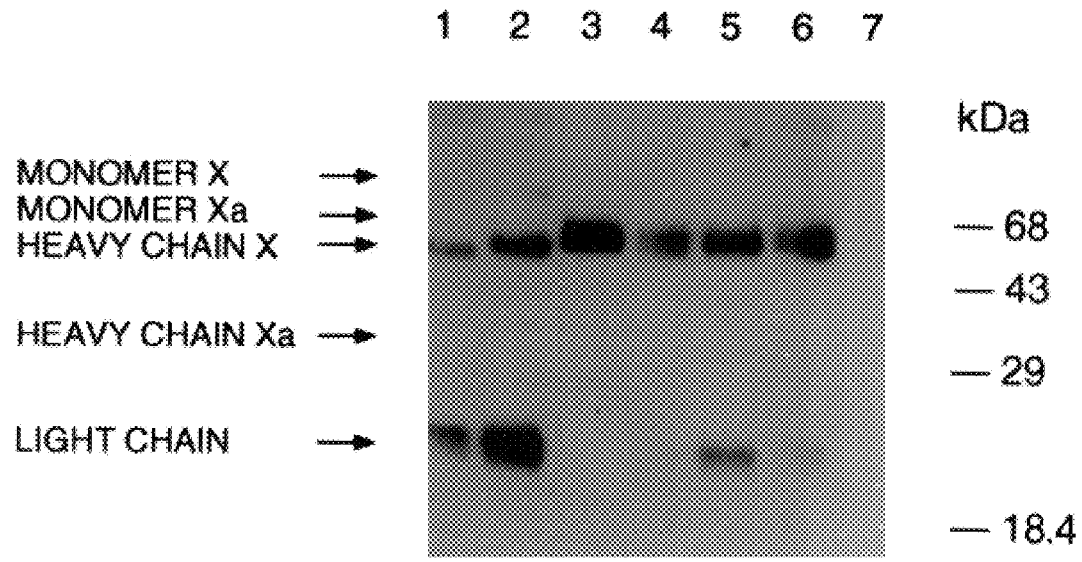
FIGS. 5a and 5b show a Western blot of recombinantly produced, potentially active Factor X and Factor Xa.
Figure 5B:
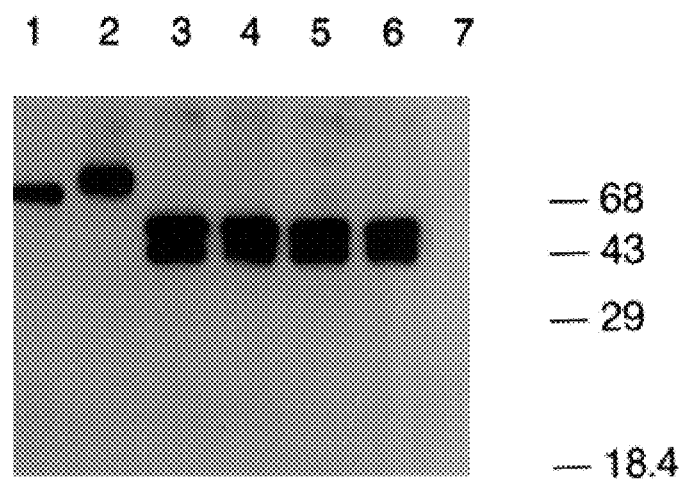

FIGS. 5a and 5b show Western blot analysis using polyclonal rabbit antisera of products derived from rX, rX'Δ0, rX'Δ1, rX'Δ2, rX'Δ3 and CHO control medium. Rabbit polyclonal antisera to X was not efficient in localizing the fully processed heavy chain of human Factor Xa; hence, in all cases the position expected to be occupied by the activated heavy chain does not appear. FIG. 5a shows reduced and FIG. 5b nonreduced forms of these recombinant proteins. Lane 1, 0.7 ,mg native human Factor X (Dr. C. Esmon, OMRF, University of Oklahoma); Lane 2, rX; Lane 3, rX'Δ0; Lane 4, rX'Δ1; Lane 5 rX'Δ2 Lane 6, rX'Δ3; Lane 7, CHO control medium.

FIG. 5a shows that the recombinant products of rX and rX'Δ2 are dimeric proteins which are separable under reducing conditions. The products of expression of rX'Δ0, rX'Δ1 and rX'Δ3 apparently are largely single chain products. It appeared that the unprocessed Factor X' single chains comigrated anomalously with the heavy chain as shown in lanes 3–7, apparently due to the degree of proteolytic processing of the novel cleavage sites. The failure of these X' precursor proteins to be processed properly was consistent with the results of a coagulation assay, described in Example 8, which demonstrated that Factor Xa, RVV-activated Factor X or recombinant Factor X and X1Δ2 were comparably active, while the remaining X' secreted products were dramatically less efficient, by at least 5 or magnitude. The data with respect to enzyme activity are shown in Table 1:

TABLE 1

| Factor X | RVV Activation | Catalytic Efficiency (%) | Coagulation |
| --- | --- | --- | --- |
| X | + | 100 | + |
| XA | − | 851 | + |
| RX | + | 29.6 | + |
| X'Δ0 | − | $5.2 \times 10^{-4}$ | − |
| X'Δ1 | − | $12.6 \times 10^{-4}$ | − |
| X'Δ2 | − | 269 | − |
| X'Δ3 | − | $69.5 \times 10^{-4}$ | − |
| CHO | − | 0 | − |

The column of Table 1 labeled "catalytic efficiency" shows the amidolytic substrate activities of the various factors, activated with RVV if necessary. The catalytic efficiencies shown are the ratio of kcat/Km and were normalized to the results for plasma Factor X. As shown in the table, both recombinant Factor X and X'Δ2 were active in Factor X dependent 2PT clotting assays, while the enzymatic activities of the other recombinant proteins were 4 orders of magnitude lower.

From FIG. 5b, it is apparent that the expression products of the X'-encoding gene are of lower molecular weight than rX or native Factor X.

EXAMPLE 5

Purification of rX and X'Δ2

Both recombinant Factor X and X'Δ2 were purified to homogeneity as follows: After growth to confluence, CHO cells transfected with pBNX or pBNX'Δ2 were washed 4–5 times with serum-free media. The cells were then cultured for consecutive 24 hr periods at 37° C. in serum-free media supplemented with 4 μg/ml vitamin K3.

Harvested media were centrifuged at 15,000× g for 20 min followed by filtration of the supernatant through a 0.2 μm filter. To the media was added Tris HCl, pH 7.5 to 20 mM, NaEDTA to 10 mM, and the resultant was chromatographed on Q-Sepharose Fast Flow (Pharmacia). All chromatographic steps were performed at 4° C. The columns were washed extensively with 20 mM Tris, pH 7.5, 10 mM EDTA, 0.15 M NaCl, and the proteins were eluted with 20 mM Tris, pH 7.5, 0.5M NaCl, 5 mM CaCl$_2$. Peak fractions were pooled and either stored frozen at −20° C. or applied directly to an anti-factor X monoclonal antibody affinity column as described by Church, W. R., et al., *Throm Res* (1985) 38:417–424. The antibody used for isolation (aHFX-Id, Mab B12-A3) is specific for human factor rX, not influenced by Ca$^{2+}$, and binds both factors X and Xa (unpublished data). Factor rX' was purified further on a benzamidine-Sepharose column (Pierce) as described by Krishnaswamy, et al., *J Biol Chem* (1987) 262:3291–3299. The concentrations of the proteins were determined by quantitative ELISA, colorimetric protein assay (Harlow, E., et al., "Antibodies, A Laboratory Manual" (1988), Cold Spring Harbor Laboratories, Cold Spring Harbor, N.Y.), and by absorbance measurement at 280 nm using extinction coefficient 11.6 and molecular weights of 58,900 for factor X, 46,000 for X'Δ2.

The purified factors, when subjected to SDS-PAGE under reducing conditions and silver stained showed that the recombinantly produced Factor X was separated into 3 bands representing the full-length precursor (75 kD), the heavy chain containing the activation peptide (45 kD) and the light chain (22 kD). When amino terminal sequence analysis was performed following electrotransfer to nylon filters, the light chain was shown to be heterogeneous with 27% initiating at Val$_{37}$ and 73% initiating at Ala$_{41}$; the 75 kD species was also heterogeneous with 41% initiating at Val$_{37}$ and 59% initiating at Ala$_{41}$.

EXAMPLE 6

Expression of Genes Encoding Inactivated Recombinant Human Factor X (rXi and rX'i)

The X' form chosen for conversion to the inactive form was the rX'Δ2 form shown in FIG. 4. pBN-derived cell lines for rX, rX' ('2), rXiN$_{88}$A$_{185}$, rXiA$_{185}$, rX'i(Δ2)N$_{88}$A$_{185}$ and rX'iN$_{88}$(Δ2) were grown to confluence in 800 cm$^2$ roller bottles as described in Example 4, washed four times with serum free medium and incubated overnight with 50 ml serum-free medium. The medium was replenished and harvested daily.

Consecutive harvests were pooled, centrifuged at 3000 rpm and passed directly through a Factor X-specific monoclonal antibody (Mab) affinity column (Mab717) supplied by Dr. C. Esmon (OMRF, University of Oklahoma). The bound "Factor X1" was eluted from the Mab717 column with 80% ethylene glycol, dialyzed against 10 mM Tris HCl, pH 7.5, 150 mM NaCl and concentrated on a Centricon 10 filtration unit (Amicon). "Factor X" protein concentrations were determined by ELISA as described in Example 4 utilizing serial dilution with comparison to a standard preparation of human Factor X (Haematologic Technologies, Inc., C. Esmon, OMRF, University of Oklahoma).

Figure 6:
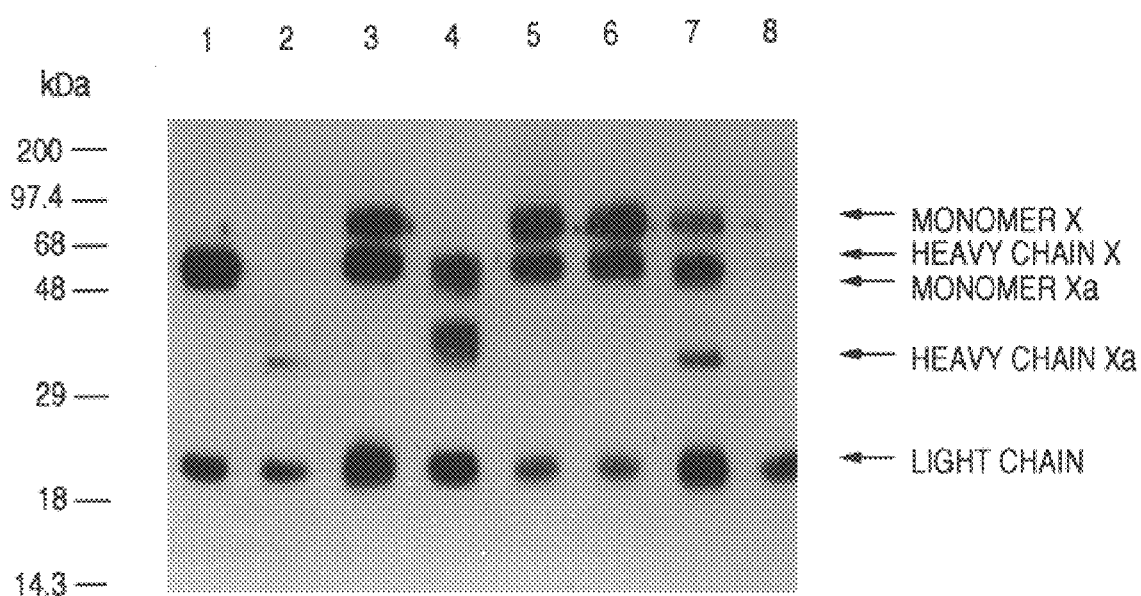
FIG. 6 is a Western blot of recombinantly produced, inactivated forms of Factor X and Factor Xa.
Figure 7A:
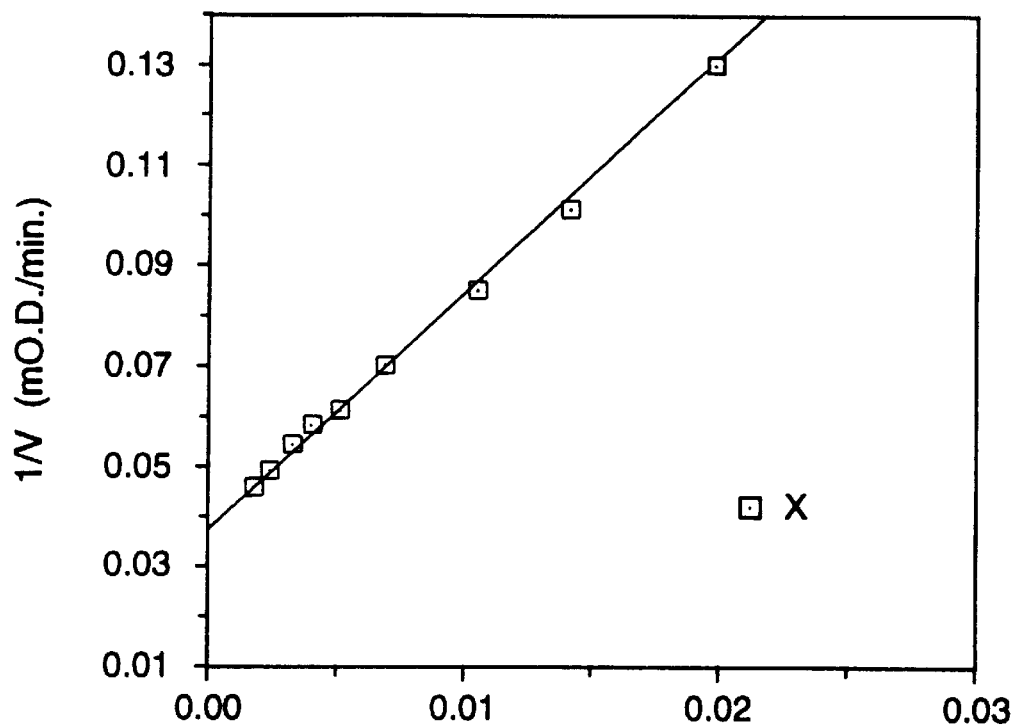
FIGS. 7a–7d consist of a series of Lineweaver-Burk plots showing the enzymatic activity of native and recombinantly produced Factor X converted to activated form.
Figure 7B:
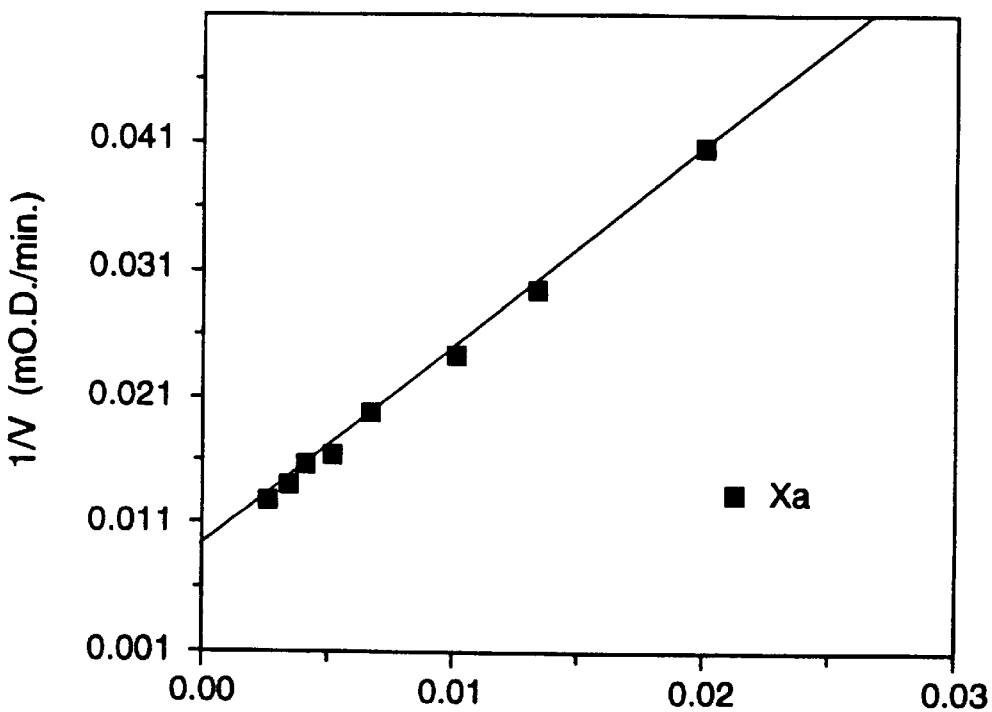
Figure 7C:
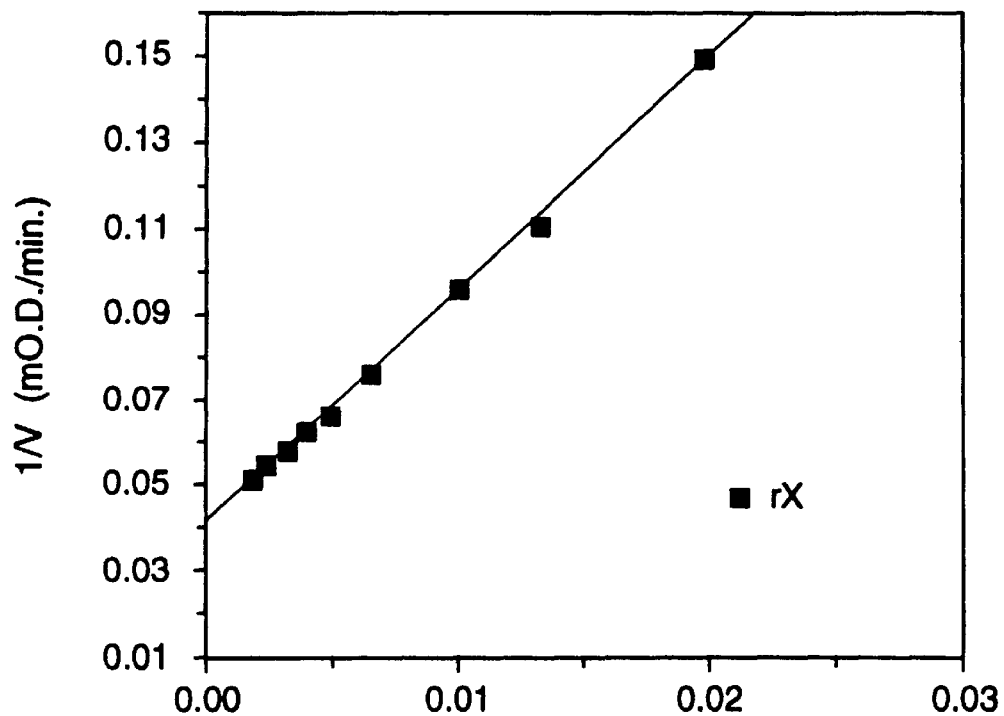
Figure 7D:
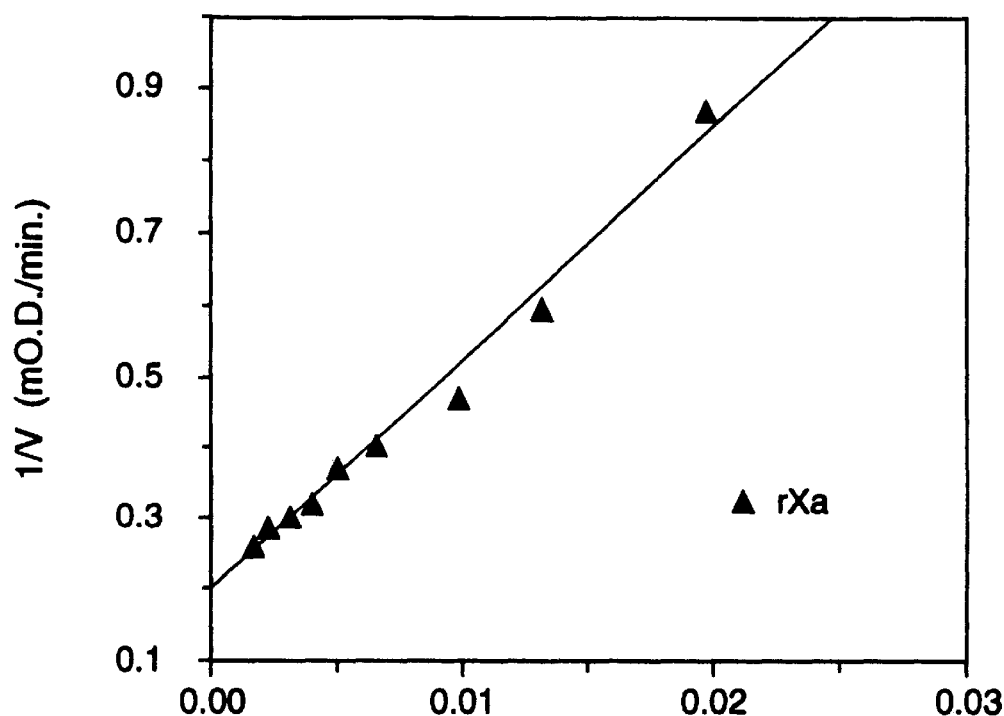

The purified proteins were characterized by Western blot analysis as outlined in Example 4. FIG. 6 shows a Western blot of these, b-mercaptoethanol-reduced, Mab717 purified recombinant human Factor X analogs. Lane 1, 0.1 mg human X (Haematologic Technologies, Inc.); Lane 2, 0.1 mg human Xa (Haematologic Technologies, Inc.); Lane 3, 0.1, mg rX; Lane 4, 0.16 mg rX'Δ2; Lane 5, 0.13 mg rXiN$_{88}$A$_{185}$; Lane 6, 0.15 mg rXiA$_{185}$; Lane 7, 0.187 mg rX'i(Δ2)N$_{88}$, Lane 8, 0.05 mg rX'i(Δ2)N$_{88}$A$_{185}$.

It is evident that, under reducing conditions, human X and human Xa are in dimeric form; human Xa shows a lower molecular weight form of the heavy chain due to the absence of the activation peptide. Recombinant human X in lane 3 is similar to native human X, however some single chain precursor is still evident. In lane 4, recombinant rX'Δ2 also shows cleavage to the heavy and light chains. In lanes 5 and 6, the modified recombinant X1 proteins behave in a manner similar to recombinant human X. As expected, lanes 7 and 8 show the presence of monomer, heavy and light chains derived from the proteolytic cleavage of X'i.

EXAMPLE 7

Enzymatic Analysis of Recombinant Human Factor X

The kinetic measurement of chromozym X (N-methoxycarbonyl-D-norleucyl-glycyl-arginine-4-nitranilide acetate, Boehringer Mannheim) hydrolysis by native human Factor X, Xa, recombinant X (rX), rX1Δ0, rX1Δ1, rX1Δ2, rX1Δ3, rXiN$_{88}$A$_{185}$, rXiN$_{88}$, rX'(Δ2N$_{88}$A$_{185}$ and inactivated bovine Xa, Xai-APMSF supplied by Dr. C. Esmon (OMRF, University of Oklahoma) (Skogen, W. F., et al, *J Biol Chem* (1984) 259:2306) were examined at room temperature in 96-well microtiter plates on a Molecular Devices Vmax spectrophotometer. The absorbance at 405 nM was monitored continuously and the reaction velocities were determined directly by the machine and plotted with the Enzfitter program (Elsevier Press). Protein concentrations were determined by ELISA (Example 6). All enzymes were diluted to the appropriate concentration in 0.1% bovine serum albumin (BSA) 50 mM Tris HCl, pH 8.0, 150 mM NaCl. Duplicate reactions were carried out in 50 mM Tris HCl, pH 8.0, 150 mM NaCl and 2.5 mM CaCl2. All recombinant human Factor X's were Mab717-purified (Example 6) except for RX'D0, RX'D1, and RX'D3 which were purified using QAE-Sepharose (Pharmacia) concentrated (Skogen, W. F., et al., *J Biol Chem* (1984) 259:2306).

The recombinantly produced peptides derived from vectors containing rX, rXiN$_{88}$A$_{185}$, rXiN$_{88}$ and rXaiN$_{88}$A$_{185}$ were treated by preincubation for 5 minutes with Russell's viper venom to convert them to the Xa or Xai form. Peptides derived from the rX'Δ0, rX'Δ1, rX'Δ2 and rX'Δ3 vectors were not treated in this fashion.

FIG. 7 is a comparison of Lineweaver-Burk plots for native human Factor X and Xa and activated forms derived from recombinant human rX and rX'. FIG. 7a, human X; FIG. 7b, human Xa; FIG. 7c, human rX (treated with Russell's viper venom protease); FIG. 7d, human rX' (not treated with protease).

Table 2 compares the Kcat and Km values of the recombinantly produced human Factor X's to the native human Factor X and Xa supplied by Haematologic Technologies, Inc.

TABLE 2

|  | Kcat (s$^{-1}$) | Km (mm) | Specificity Constant Kcat/Km (s$^{-1}$M$^{-1}$) |
|---|---|---|---|
| Native Forms |  |  |  |
| X | 64 | 131 | 489 × 10$^3$ |
| Xa | 367 | 184 | 1996 × 10$^3$ |
| Precursor construct |  |  |  |
| rX | 22 | 134 | 167 × 10$^3$ |
| rX'Δ1 | N.D. | — | — |
| rX'Δ2 | N.D. | — | — |
| rX'Δ3 | 17 | 149 | 115 × 10$^3$ |
| rXiN$_{88}$Aa$_{185}$ | N.D. | — | — |
| rXiA$_{185}$ | N.D. | — | — |
| rX'iN$_{88}$A$_{185}$ | N.D. | — | — |
| rX'iN$_{88}$ | N.D. | — | — |
| Control CHO medium | N.D. | — | — |

N.D. = not detected, Kcat ≤ .1 in 14 hrs–16 hrs assay.

Of course, none of the inactivated forms give values; of the rX' forms, only rX'Δ2 showed activity.

EXAMPLE 8

Factor X Dependent Prothrombinase Complex Activity of Human X, Xa and Recombinant Human rX and rX'

Factor X dependent prothrombinase complex activity was determined by measuring the rate of chromozyme TH (tosyl-glycyl-prolyl-arginine-4 nitroanilide acetate, Boehringer Mannheim) hydrolysis by thrombin at room temperature in a 96-well microtiter plate on a Molecular Devices Vmax spectrophotometer. The absorbance at 405 nM was continuously monitored and the initial one minute reaction velocities were determined directly by the machine and plotted using the Enzfitter program (Elsevier). Reaction mixtures were performed in triplicate with 0.05×10$^{-4}$ M to 1.5×10$^{-9}$ M "Factor X," determined by ELISA (Example 6), 0.5×10$^{-6}$ M human prothrombin (STAGO, American Diagnostics, Inc.) 7.5×10$^{-9}$ M human factor Va (Haematologic Technologies, Inc.), 20×10$^{-6}$ M phosphocholine/phosphoserine 75%/25% (PCPS) (supplied by Dr. W. R. Church, University of Vermont), or equivalent amounts of rabbit brain cephalin (Sigma) (Example 9), 0.1% BSA (Sigma), 0.1×10$^{-3}$ M chromozym TH (Boehringer Mannheim), 25 mM Tris HCl, pH 7.5, 150 mM NaCl and 5 mM CaCl2.

Figure 8A:
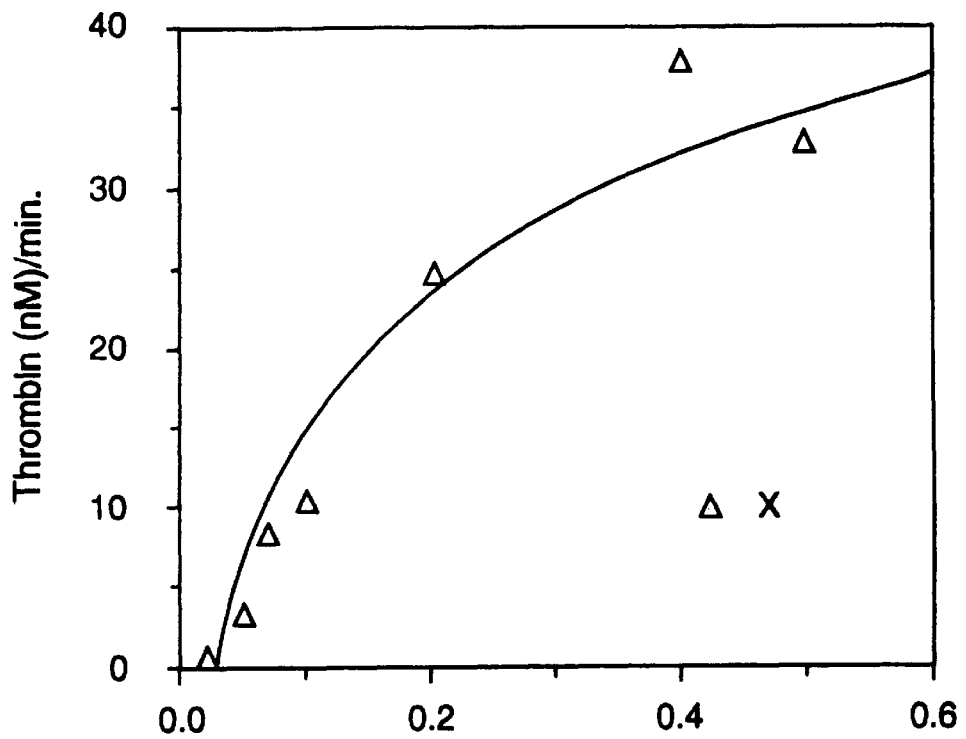
FIGS. 8a–8d show a comparison of prothrombinase complex activity of various Factor X forms.
Figure 8B:
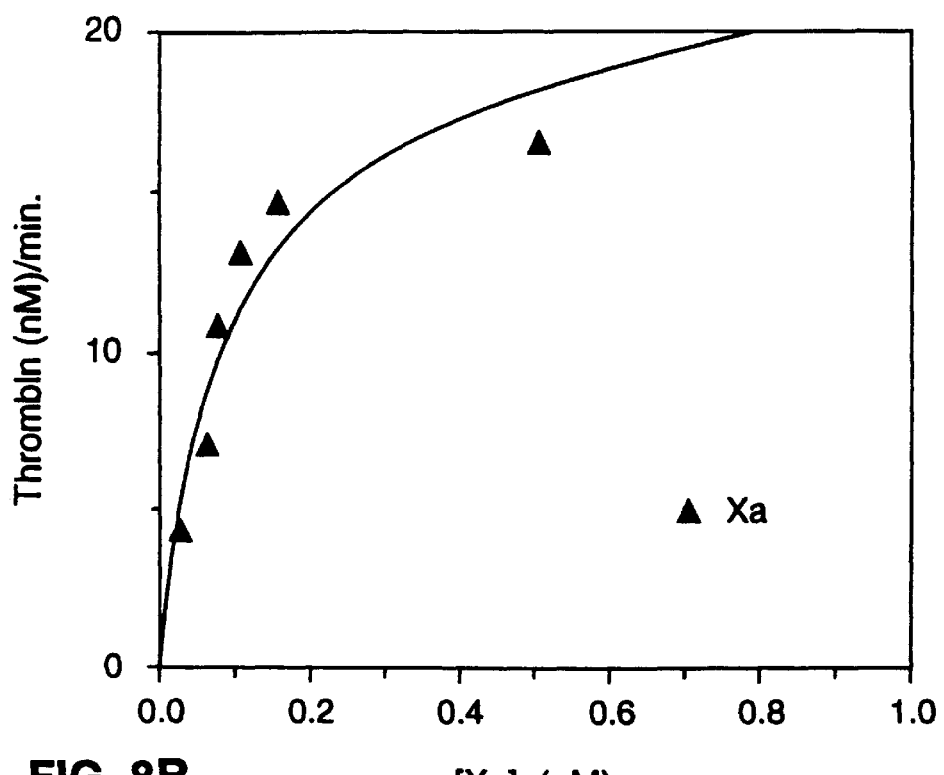
Figure 8C:
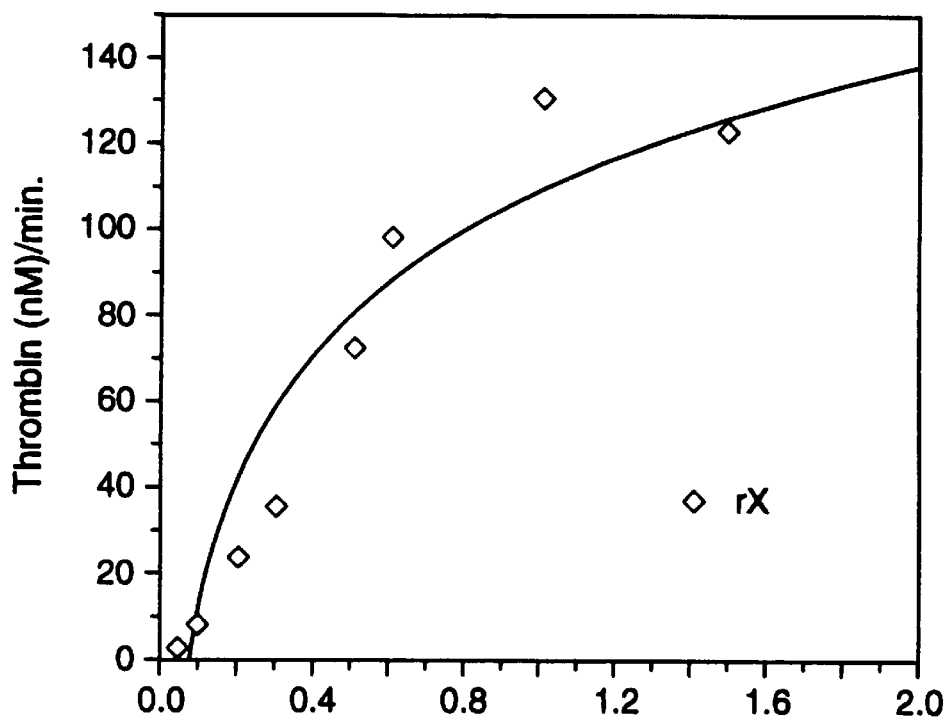
Figure 8D:
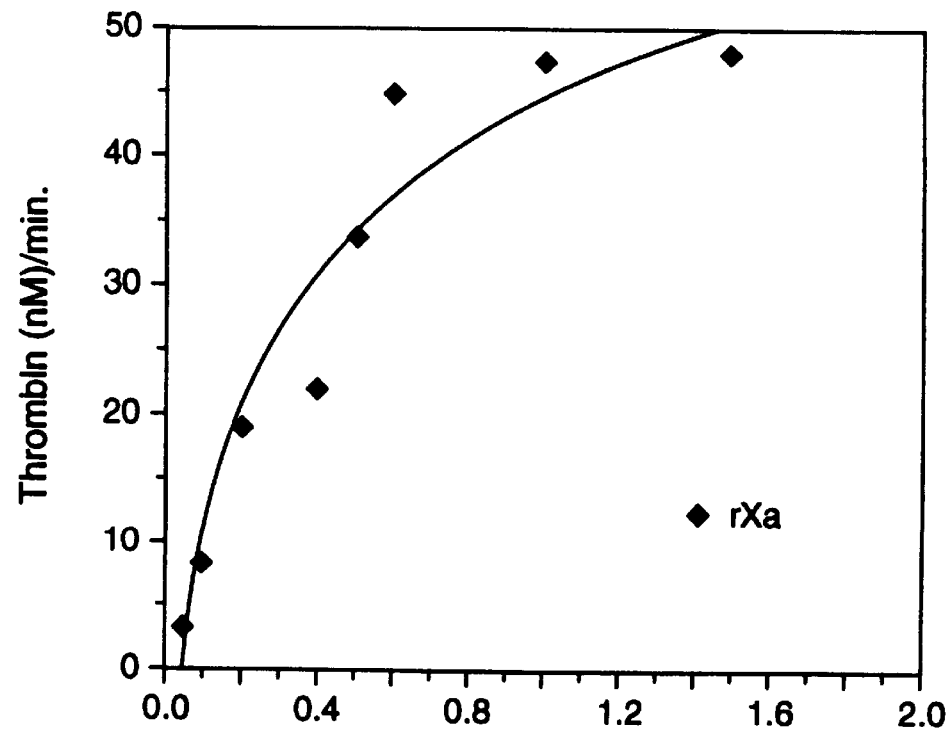

Human Factor rX and rX' dependent prothrombinase complex activity utilized PCPS and human Factor X and Xa dependent prothrombinase complex activity utilized cephalin. Human Factor X and rX were preincubated for 5 minutes with Russell's viper venom (Haematologic Technologies, Inc.). Thrombin hydrolysis of chromozym TH as determined by increase of fluorescence signal, was linear throughout the experimental protocol. No observable rates were shown for rXiN$_{88}$A185 at 59.2×10$^{-4}$ M, rX'iN$_{88}$A$_{185}$ at 10.2×10$^{-9}$ M, or for bXaiAPMSF at 1×10$^{-9}$ M. FIGS. 8a–8d compare Factor X dependent prothrombinase complex activity of human X (FIG. 8a), human Xa (FIG. 8b) (Haematologic Technologies, Inc.), recombinant human rX (after treatment with protease) (FIG. 8c) and recombinant human rX'Δ2 (after no protease treatment) (FIG. 8d). All are comparably active.

EXAMPLE 9

Coagulation of Plasma

Figure 9:
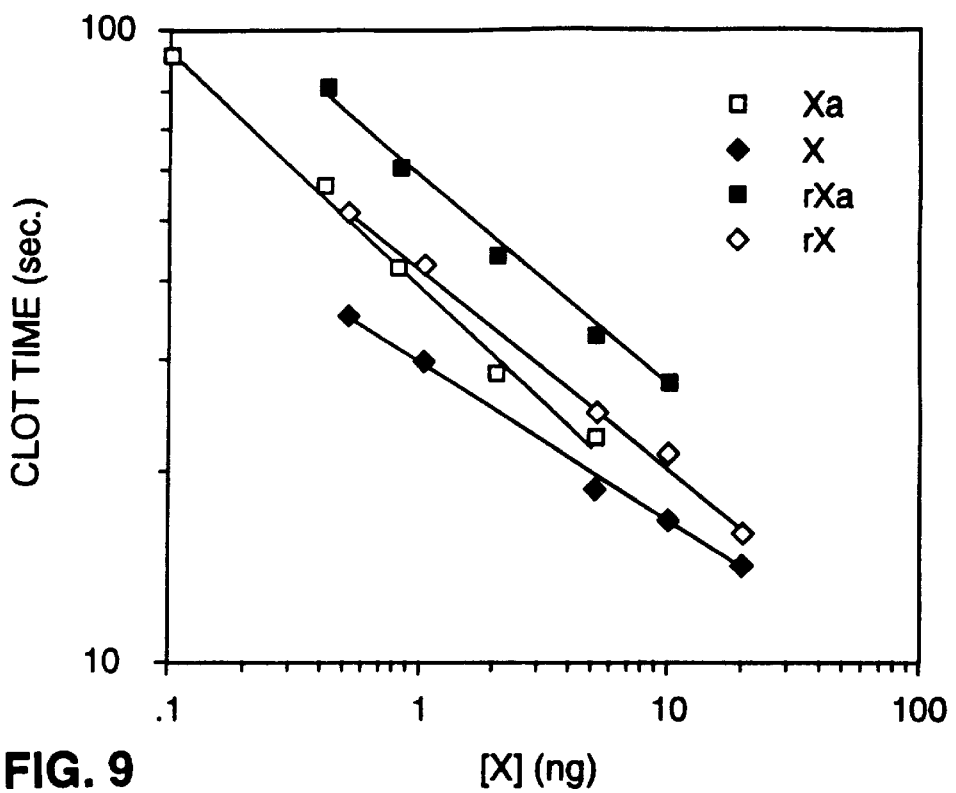
FIG. 9 shows the result of a two-stage prothrombin clotting assay for various forms of Factor X.

Mab717 purified rX and rXa were assayed for plasma coagulation activity in an automated two-stage prothrombin assay on a MLA Electra 800 fibrometer. Enzyme protein concentrations were determined by ELISA (Example 6) and diluted in 0.1% BSA, 150 mM NaCl prior to use. Bovine Factor X and Factor VII deficient plasma (Sigma) and rabbit brain cephalin (sigma) were prepared according to manufacturers' instructions. Russell's viper venom 0.1 μg/ml was added to human X and rX assays. The reaction mixture comprised 0.1 ml Factor X, 0.1 ml 150 mM NaCl, 0.1 ml cephalin and 0.1 ml 25 mM CaCl2. Duplicates were performed on each concentration and the average of two experiments were calculated. FIG. 9 compares the plasma coagulation activity of human X, human Xa, human rX and human rXa. Human rX was calculated to be 45% as active as human X and human rXa was calculated to be 32% as active as human Xa.

EXAMPLE 10

Inhibition of Prothrombinase Complex Activity by rXiN$_{88}$A$_{185}$. Human rX'i)Δ2)N$_{88}$A$_{185}$ and Bovine bXai-APMSF Inhibition of native human Factor X dependent prothrombinase complex activity by human rXiN$_{88}$A$_{185}$ and inhibition of native human Factor 5×10$^{-9}$ M Xa dependent prothrombinase complex activity by human rXi (Δ2)N$_{88}$A$_{185}$ (rXai) and bovine bXai-APMSF (C. Esmon, OMRF, University of Oklahoma) was tested as detailed in Example 8. It is necessary to compare directly X with Xi and Xa with Xai because of kinetic factors and the strength of the complex once formed. Human rXiN$_{88}$A$_{815}$ was preincubated for 5 minutes with 0.1 mg/ml Russell's viper venom. The human Factor X and Xa concentrations were 1×10$^9$M.

Figure 10:
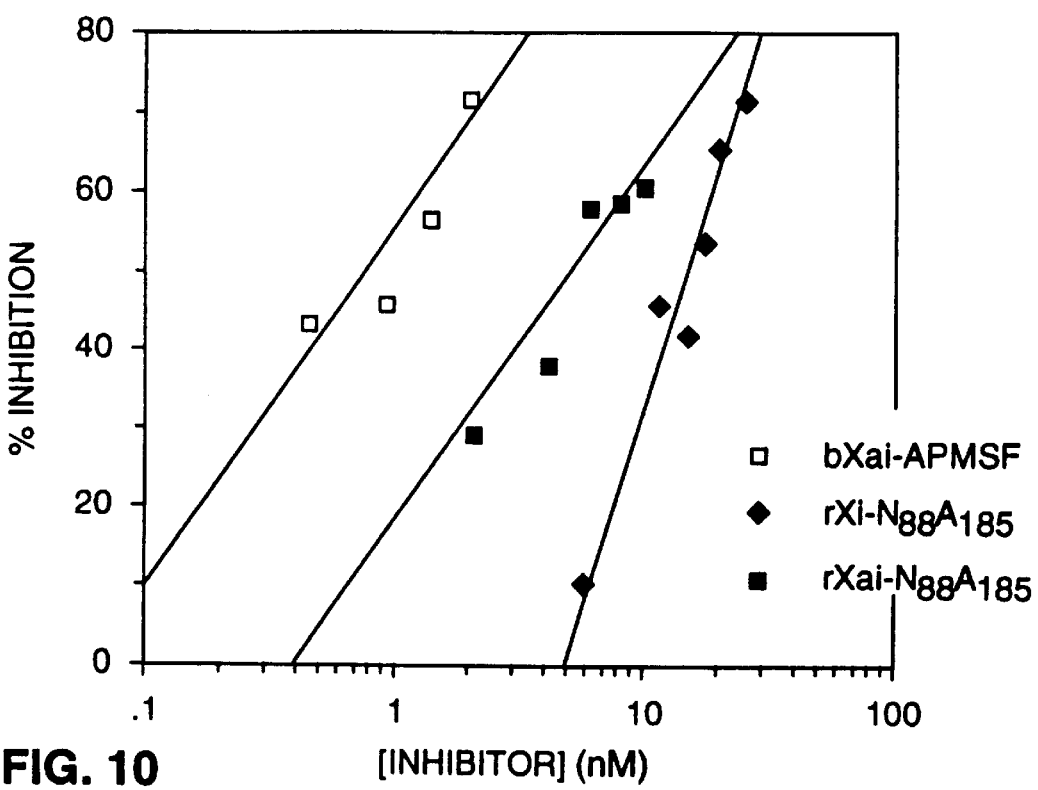
FIG. 10 shows inhibition of prothrombinase complex formation by inactive forms of Factor X.

FIG. 10 shows the concentration dependent inhibition of the human Factor Xa dependent prothrombinase complex by bXai-APMSF, rX'i(Δ2)N$_{88}$A$_{185}$(rXai) and inhibition of the human Factor X dependent prothrombinase complex by rXiN$_{88}$A$_{185}$. 50% inhibition by bXai-APMSF was obtained at 0.9×10$^{-9}$ M, 50% inhibition by rX'i(Δ2)N$_{88}$A$_{185}$ was obtained at 6×10$^{-9}$M and 50% inhibition by rXiN$_{88}$A$_{185}$ was obtained at 10.6×10$^{-9}$M.

EXAMPLE 11

Preparation of Acylated Factor Xa

Figure 11:
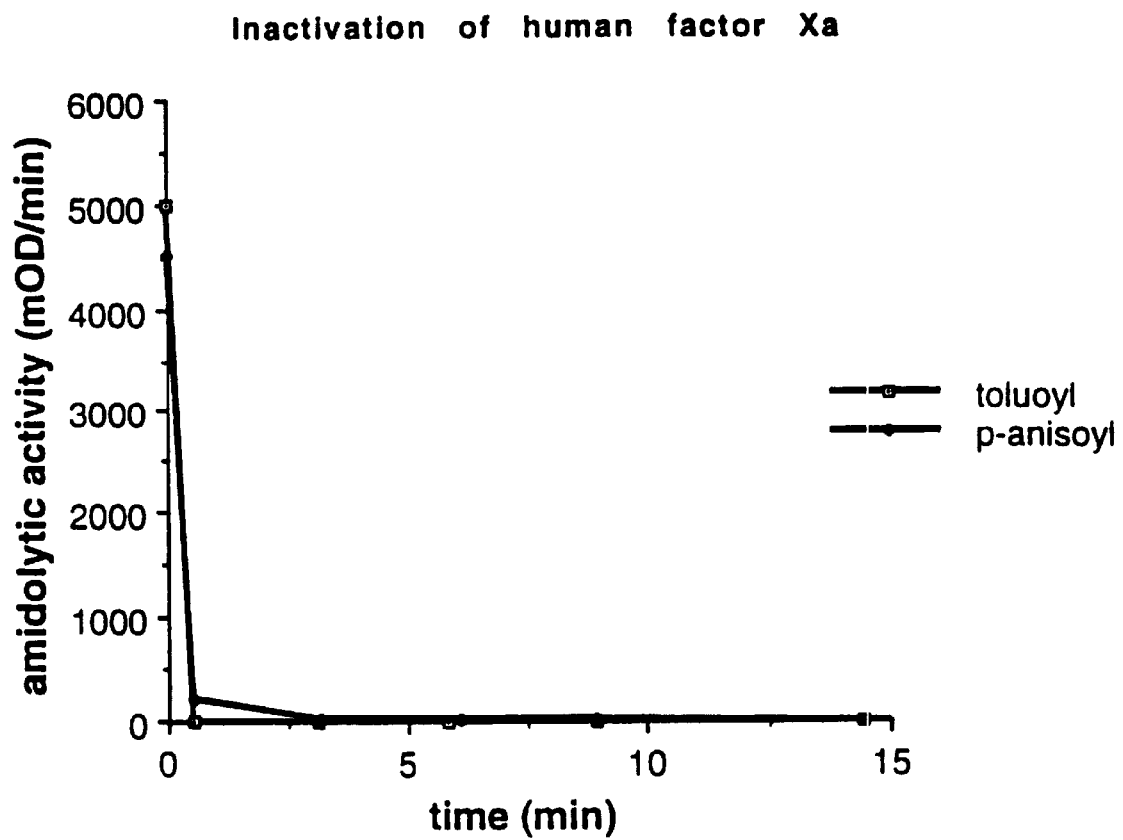
FIG. 11 shows residual amidolytic activity of human factor Xa after acylation.

Human factor Xa was prepared as described above, and treated with a 3 fold molar excess of p-amidinophenyl p'-anisate or p-amidinophenyl p'-toluate. At different time points, an aliquot was removed from the reaction mixture and assayed for factor Xa dependent amidolytic activity. The plot in FIG. 11 depicts residual amidolytic activity versus time of chemical modification.

Figure 12A:
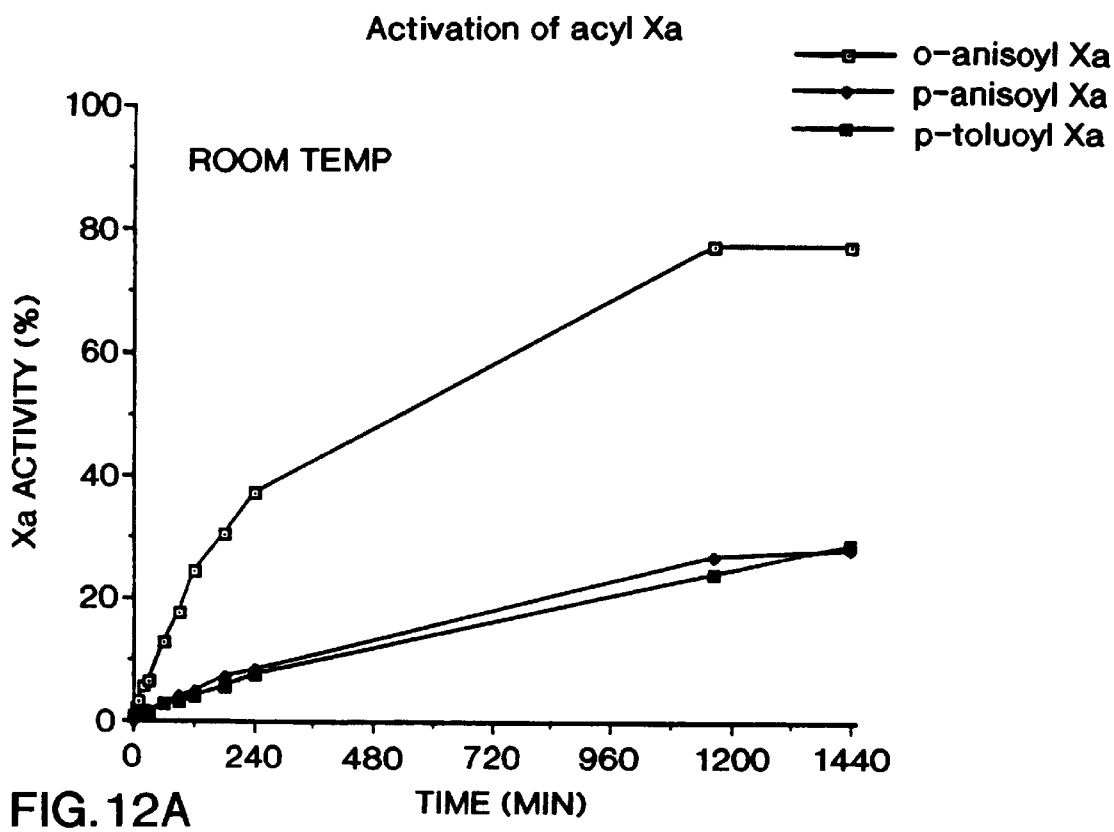
FIGS. 12a and 12b shows the activation of acyl Xa.
Figure 12B:
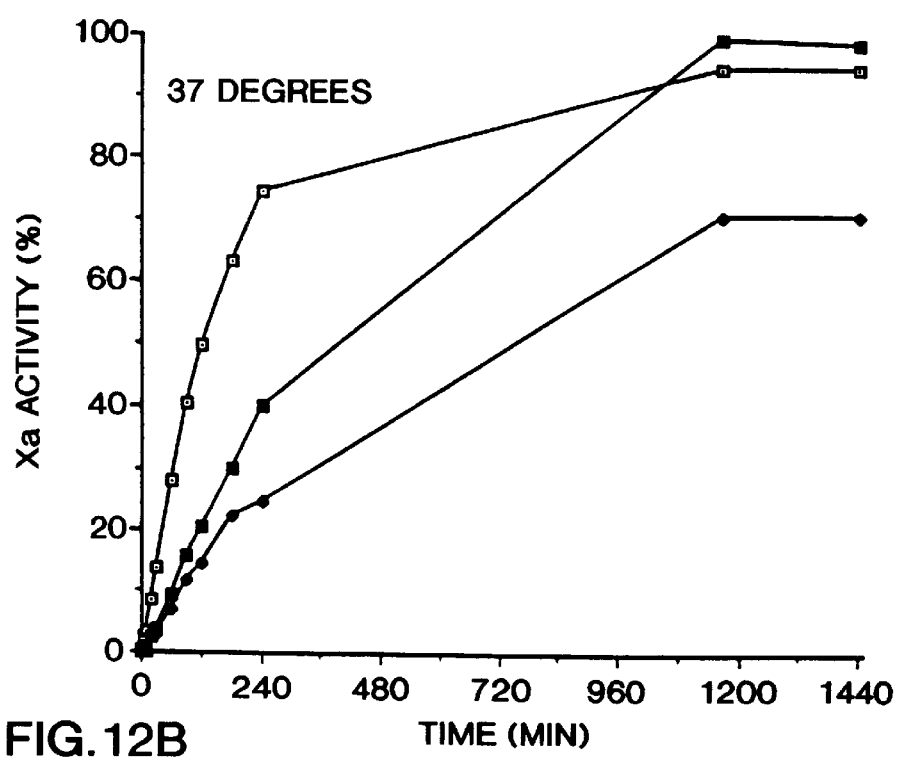

Next, evaluations were made of the activation of the acyl Xa. Acylated factor Xa was incubated in a buffer at pH 7.5 at room temperature or 37° C. Over the time course of experimentation, withdrawn aliquots were assayed for factor Xa activity. A sample of unmodified human factor Xa was subjected to the same incubation protocol. FIGS. 12a and 12b depict the relative percent activity of incubated acyl Xa.

EXAMPLE 12

Clotting Activities of acyl-Xa

Acylated inactive human Factor Xa (acyl-Xa) was prepared as described above, and its in vitro and in vivo properties were studied. It was found that acyl-Xa deacylates and regains factor Xa catalytic activity in a time-dependent manner. Recovery rates were influenced by the structure of the acyl-leaving group, temperature and pH. Deacylated Factor Xa demonstrated normal amidolytic, prothrombinase and plasma clotting activities in vitro. In vivo bolus administration of anisoyl-Xa (p-amidinophenyl p'anisate) at 2, 10, and 50 μg/kg in normal rabbits, dogs and hemophilic dogs demonstrated dose-dependent procoagulent activity as measured by APTT and PT clotting times (data not shown). Procoagulant activity was time-dependent and correlated with circulating plasma levels. No significant changes in other hemostatic parameters were observed (TCT, Fibrinogen, FVIII, FIX, CBC).

Figure 13:
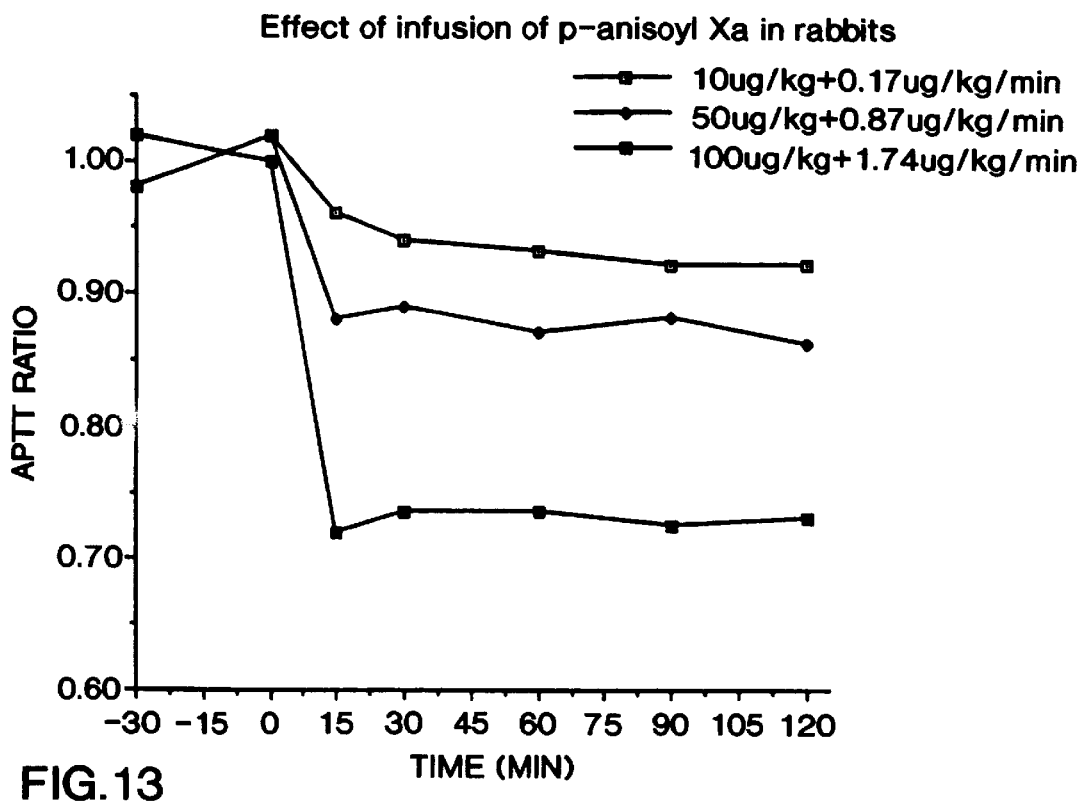
FIG. 13 shows the effect of infusion of p-anisoyl factor Xa in rabbits.

The effects of infusion of p-anisoyl Xa in rabbits was also studied. Acyl Xa was infused into anesthetized New Zealand rabbits. Infusion continued for two hours and blood samples were collected from the femoral vein at different time points during this period. FIG. 13 depicts ex-vivo clotting (APTT) over the time course of infusion. The ratios are expressed relative to pre drug control.

EXAMPLE 13

Activation of other acylated proteins

Figure 14:
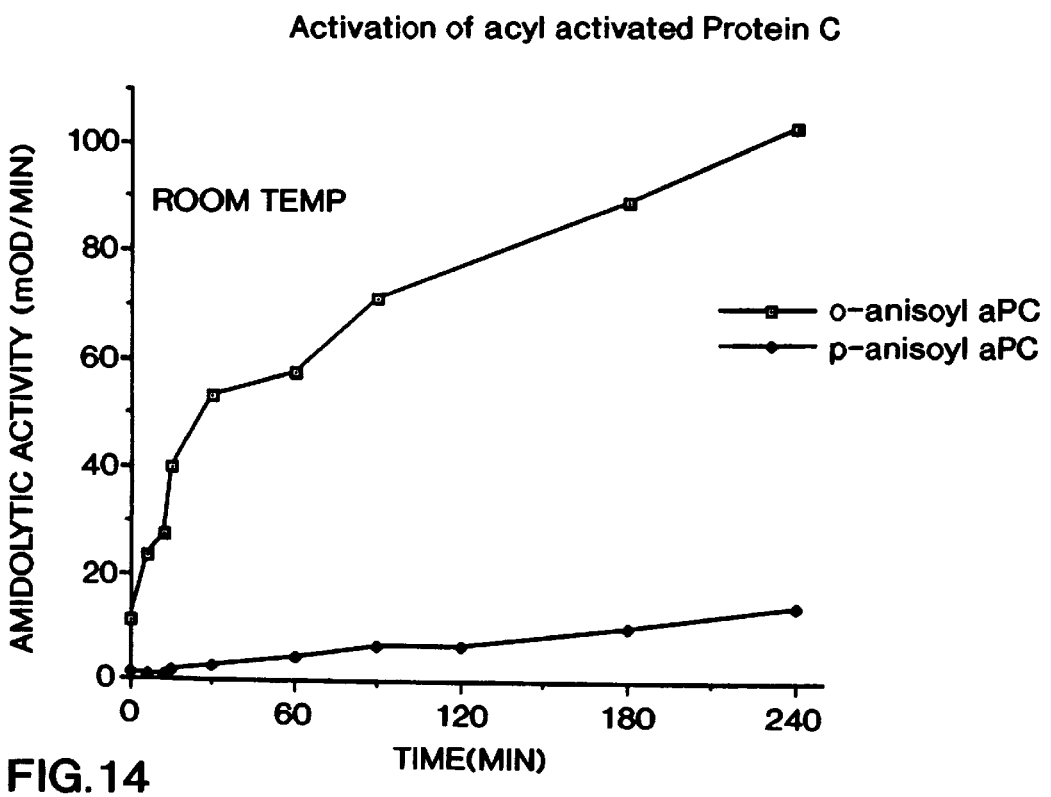
FIG. 14 shows the activation of acyl activated protein C.

Activation of acyl activated protein C is shown in FIG. 14. Acylated aPC prepared as described above was incubated in a buffer at pH 7.5 at room temperature. Over the time course of experimentation, withdrawn aliquots are assayed for aPC activity in a chromogenic assay. A sample of unmodified human aPC was subjected to the same incubation protocol. FIG. 14 depicts the relative percent activity in incubated acyl aPC versus control aPC.

Figure 15:
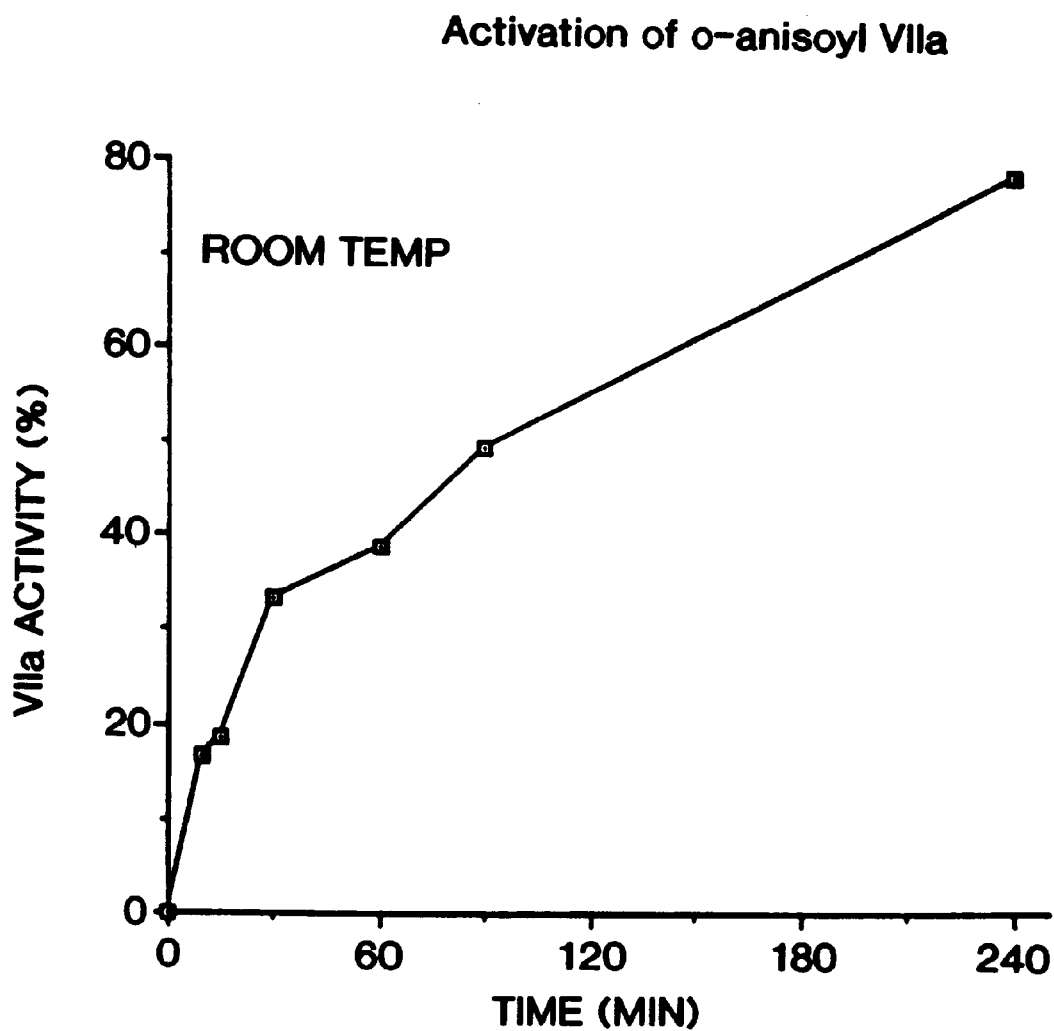
FIG. 15 shows the activation of o-anisoyl factor VIIa.

Activation of o-anisoyl factor VIIa is shown in FIG. 15. Acylated factor VIIa was prepared as described above and incubated in buffer at a protein concentration of 160 nM. At each time point an aliquot was diluted to 0.16 nM and incubated with lipidated tissue factor (0.25 nM) for one minute at room temperature. The factor VIIa/Tissue Factor mixture was then used for activation of factor X and the resulting factor Xa was assayed in an amidolytic assay. Results are shown in FIG. 15.

We claim:

1. An indwelling intravascular device comprising a procoagulant composition comprising Factor Xa and biologically active polypeptide fragments thereof, which Factor Xa and fragments thereof have been transiently inactivated to have little or no enzymatic activity, and wherein said inactivated Factor Xa and fragments thereof generate an active form of Factor Xa in the presence of serum.

2. The indwelling intravascular device of claim 1, wherein the Factor Xa or fragments thereof comprises a consecutive sequence of at least 5, 10, 15, 20, 25, 30 or 40 amino acids of Factor Xa.

3. The indwelling intravascular device of claim 2, wherein said device is selected from the group consisting of i.v.s, patch, tubing, vascular stent, catheter and vascular graft.

4. The indwelling intravascular device of claim 2, wherein the Factor Xa or fragments thereof are transiently inactivated by an antibody or antibody fragment thereof.

5. The indwelling intravascular device of claim 4, wherein said antibody is a monoclonal antibody.

6. The indwelling intravascular device of claim 4, wherein the antibody fragment is a Fab fragment.

7. The indwelling intravascular device of claim 2, wherein the Factor Xa or fragments thereof are transiently inactivated by an inhibitor selected from the group consisting of benzamidines, substituted benzamidines and Kunitz class inhibitors.

8. The indwelling intravascular device of claim 7, wherein the inhibitor is a Kunitz class inhibitor and is further selected from the group consisting of aprotinin and LACI.

9. The indwelling intravascular device of claim 2, wherein the Factor Xa and fragments thereof are transiently inactivated by 1,2-bis(5-amidino 2-benzofuranyl)ethane.

10. The indwelling intravascular device of claim 2, wherein the Factor Xa and fragments thereof are transiently inactivated by an acyl group.

11. The indwelling intravascular device of claim 10, wherein the Factor Xa and fragments thereof are transiently inactivated by an acyl group selected from the group consisting of unsubstituted and substituted benzoyl, unsubstituted and substituted acryloyl with the proviso that the substituted acryloyl is not a phenyl substituted acryloyl, unsubstituted and substituted acetyl, unsubstituted and substituted carbonyl, and unsubstituted and substituted isocoumarins.

12. The indwelling intravascular device of claim 10, wherein the acyl group is an unsubstituted or substituted benzoyl selected from the group consisting of benzoyl, p-fluoro benzoyl, o-fluoro benzoyl, p-alkoxy benzoyl, o-alkoxy benzoyl, 4-amino benzoyl, 4N,N-dimethylamino benzoyl, 4N-(2-N'-(3-(2-pyridyldithio)-propenyl)aminoethyl)amino benzoyl, guanidino benzoyl, 4-amidinophenyl-p-anisoyl, p-anisoyl, o-anisoyl, 4-amidinophenyl-p-toluoyl, p-toluoyl and o-toluoyl.

13. The indwelling intravascular device of claim 10, wherein the acyl group is an unsubstituted or non-phenyl substituted acryloyl selected from the group consisting of 3,3-dimethyl acryloyl, 3,4-dimethyl acryloyl, 3,3-difluoro acryloyl and 3,4-difluoro acryloyl.

14. The indwelling intravascular device of claim 10, wherein the acyl group is an unsubstituted or substituted acetyl selected from the group consisting of cyclohexylidine acetyl, 1-methylcyclohexylidine acetyl, methyl phenyl ketone and acetanilide.

15. The indwelling intravascular device of claim 10, wherein the acyl group is an unsubstituted carbonyl of cyclohex-1-ene carbonyl.

16. The indwelling intravascular device of claim 10, wherein the acyl group is an unsubstituted or substituted isocoumarin selected from the group consisting of 3-alkoxy 4-chloroisocoumarins.

* * * * *